(12) United States Patent
Estes et al.

(10) Patent No.: US 7,708,717 B2
(45) Date of Patent: May 4, 2010

(54) OPERATING AN INFUSION PUMP SYSTEM

(75) Inventors: Mark C. Estes, Simi Valley, CA (US);
Mitchell Wenger, Chicago, IL (US);
Morten Mernoe, Charlottenlund (DK);
James Causey, Simi Valley, CA (US);
Todd Kirschen, Fullerton, CA (US)

(73) Assignee: M2 Group Holdings, Inc., Sunnyvale, CA (US)

( * ) Notice: Subject to any disclaimer, the term of this patent is extended or adjusted under 35 U.S.C. 154(b) by 380 days.

(21) Appl. No.: 11/686,704

(22) Filed: Mar. 15, 2007

(65) Prior Publication Data
US 2007/0173762 A1 Jul. 26, 2007

Related U.S. Application Data

(63) Continuation of application No. 11/522,603, filed on Sep. 18, 2006.

(60) Provisional application No. 60/720,411, filed on Sep. 26, 2005, provisional application No. 60/720,405, filed on Sep. 26, 2005, provisional application No. 60/721,267, filed on Sep. 28, 2005.

(51) Int. Cl.
*A61M 1/00* (2006.01)
*A61M 5/00* (2006.01)
*A61K 9/22* (2006.01)
(52) U.S. Cl. ............ 604/151; 604/890.1; 604/232
(58) Field of Classification Search ............ 604/131, 604/232, 890.1, 151, 152, 65–67
See application file for complete search history.

(56) References Cited

U.S. PATENT DOCUMENTS

| | | | |
|---|---|---|---|
| 2,605,765 A | 8/1952 | Kollsman | |
| 3,886,938 A | 6/1975 | Szabo et al. | |
| 4,077,405 A | 3/1978 | Haerten et al. | |
| 4,231,368 A | 11/1980 | Becker | |
| 4,265,241 A | 5/1981 | Portner et al. | |
| 4,300,554 A | 11/1981 | Hessberg et al. | |
| 4,313,439 A | 2/1982 | Babb et al. | |
| 4,373,527 A | 2/1983 | Fischell | |

(Continued)

FOREIGN PATENT DOCUMENTS

CA    2543545    5/2005

(Continued)

OTHER PUBLICATIONS

Accu-Chek Spirit, "Pump Therapy Made for You," Roche, 2006, 6 pages.

(Continued)

*Primary Examiner*—Nicholas D Lucchesi
*Assistant Examiner*—Rebecca E Eisenberg
(74) *Attorney, Agent, or Firm*—Fish & Richardson P.C.

(57) ABSTRACT

Some embodiments of a medical infusion pump system include a pump device and a removable controller device. When the pump device and the removable controller device are removably attached to one another, the components may provide a portable infusion pump unit to dispense medicine to a user. In particular embodiments, the removable controller device includes a user interface to readily provide information, for example, about the operation of the pump.

25 Claims, 12 Drawing Sheets

U.S. PATENT DOCUMENTS

| | | | |
|---|---|---|---|
| 4,398,908 A | 8/1983 | Siposs | |
| 4,435,173 A | 3/1984 | Siposs et al. | |
| 4,443,218 A | 4/1984 | DeCant, Jr. et al. | |
| 4,493,704 A | 1/1985 | Beard et al. | |
| 4,529,401 A | 7/1985 | Leslie et al. | |
| 4,619,653 A | 10/1986 | Fischell | |
| 4,850,817 A | 7/1989 | Nason et al. | |
| 4,902,278 A | 2/1990 | Maget et al. | |
| 5,045,064 A | 9/1991 | Idriss | |
| 5,088,981 A | 2/1992 | Howson et al. | |
| 5,190,522 A | 3/1993 | Wojcicki et al. | |
| 5,250,027 A | 10/1993 | Lewis et al. | |
| 5,261,882 A | 11/1993 | Sealfon et al. | |
| 5,314,412 A | 5/1994 | Rex | |
| 5,335,994 A | 8/1994 | Weynant | |
| 5,338,157 A | 8/1994 | Blomquist | |
| 5,342,180 A | 8/1994 | Daoud | |
| 5,395,340 A | 3/1995 | Lee | |
| 5,411,487 A | 5/1995 | Castagna | |
| 5,545,143 A | 8/1996 | Fischell et al. | |
| 5,551,850 A | 9/1996 | Williamson et al. | |
| 5,569,186 A | 10/1996 | Lord et al. | |
| 5,626,566 A | 5/1997 | Petersen et al. | |
| 5,637,095 A | 6/1997 | Nason et al. | |
| 5,665,065 A | 9/1997 | Colman et al. | |
| 5,718,562 A | 2/1998 | Lawless | |
| 5,741,216 A | 4/1998 | Hemmingsen et al. | |
| 5,764,034 A | 6/1998 | Bowman et al. | |
| 5,772,635 A | 6/1998 | Dastur et al. | |
| 5,816,306 A | 10/1998 | Giacomel | |
| 5,852,803 A | 12/1998 | Ashby, III et al. | |
| 5,919,167 A | 7/1999 | Mulhauser et al. | |
| 5,925,018 A | 7/1999 | Ungerstedt | |
| 5,928,201 A | 7/1999 | Poulsen et al. | |
| 5,947,934 A | 9/1999 | Hansen et al. | |
| 5,951,530 A | 9/1999 | Steengaard et al. | |
| 5,957,889 A | 9/1999 | Poulsen et al. | |
| 5,984,894 A | 11/1999 | Poulsen et al. | |
| 5,984,897 A | 11/1999 | Petersen et al. | |
| 5,997,475 A | 12/1999 | Bortz | |
| 6,003,736 A | 12/1999 | Ljunggren | |
| 6,010,485 A | 1/2000 | Buch-Rasmussen et al. | |
| 6,033,377 A | 3/2000 | Rasmussen et al. | |
| 6,045,537 A | 4/2000 | Klitmose | |
| 6,074,372 A | 6/2000 | Hansen | |
| 6,110,149 A | 8/2000 | Klitgaard et al. | |
| 6,127,061 A | 10/2000 | Shun et al. | |
| 6,156,014 A | 12/2000 | Petersen et al. | |
| 6,171,276 B1 | 1/2001 | Lippe et al. | |
| 6,231,540 B1 | 5/2001 | Smedegaard | |
| 6,248,067 B1 | 6/2001 | Causey, III et al. | |
| 6,248,090 B1 | 6/2001 | Jensen et al. | |
| 6,248,093 B1 | 6/2001 | Moberg | |
| 6,277,098 B1 | 8/2001 | Klitmose et al. | |
| 6,302,855 B1 | 10/2001 | Lav et al. | |
| 6,302,869 B1 | 10/2001 | Klitgaard | |
| 6,375,638 B2 | 4/2002 | Nason et al. | |
| 6,379,339 B1 | 4/2002 | Klitgaard et al. | |
| 6,381,496 B1 | 4/2002 | Meadows et al. | |
| 6,404,098 B1 | 6/2002 | Kayama et al. | |
| 6,427,088 B1 | 7/2002 | Bowman, IV et al. | |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,491,684 B1 | 12/2002 | Joshi et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,577,899 B2 | 6/2003 | Lebel et al. | |
| 6,582,404 B1 | 6/2003 | Klitgaard et al. | |
| 6,585,644 B2 | 7/2003 | Lebel et al. | |
| 6,585,699 B2 | 7/2003 | Ljunggreen et al. | |
| 6,605,067 B1 | 8/2003 | Larsen | |
| 6,613,019 B2 | 9/2003 | Munk | |
| 6,641,533 B2 | 11/2003 | Causey, III et al. | |
| 6,648,821 B2 | 11/2003 | Lebel et al. | |
| 6,650,951 B1 | 11/2003 | Jones et al. | |
| 6,656,158 B2 | 12/2003 | Mahoney et al. | |
| 6,656,159 B2 | 12/2003 | Flaherty | |
| 6,659,948 B2 | 12/2003 | Lebel et al. | |
| 6,659,978 B1 | 12/2003 | Kasuga et al. | |
| 6,659,980 B2 | 12/2003 | Moberg et al. | |
| 6,663,602 B2 | 12/2003 | Møller | |
| 6,668,196 B1 | 12/2003 | Villegas et al. | |
| 6,669,669 B2 | 12/2003 | Flaherty et al. | |
| 6,687,546 B2 | 2/2004 | Lebel et al. | |
| 6,690,192 B1 | 2/2004 | Wing | |
| 6,691,043 B2 | 2/2004 | Ribeiro, Jr. | |
| 6,692,457 B2 | 2/2004 | Flaherty | |
| 6,692,472 B2 | 2/2004 | Hansen et al. | |
| 6,694,191 B2 | 2/2004 | Starkweather et al. | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,198 B2 | 4/2004 | Larsen | |
| 6,723,072 B2 | 4/2004 | Flaherty et al. | |
| 6,733,446 B2 | 5/2004 | Lebel et al. | |
| 6,736,796 B2 | 5/2004 | Shekalim | |
| 6,740,059 B2 | 5/2004 | Flaherty | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,749,587 B2 | 6/2004 | Flaherty | |
| 6,752,787 B1 | 6/2004 | Causey, III et al. | |
| 6,758,810 B2 | 7/2004 | Lebel et al. | |
| 6,768,425 B2 | 7/2004 | Flaherty et al. | |
| 6,780,156 B2 | 8/2004 | Haueter et al. | |
| 6,786,246 B2 | 9/2004 | Ohms et al. | |
| 6,786,890 B2 | 9/2004 | Preuthun et al. | |
| 6,796,970 B1 | 9/2004 | Klitmose et al. | |
| 6,799,149 B2 | 9/2004 | Hartlaub | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,827,702 B2 | 12/2004 | Lebel et al. | |
| 6,830,558 B2 | 12/2004 | Flaherty et al. | |
| 6,852,104 B2 | 2/2005 | Blomquist | |
| 6,854,620 B2 | 2/2005 | Ramey | |
| 6,854,653 B2 | 2/2005 | Eilersen | |
| 6,855,129 B2 | 2/2005 | Jensen et al. | |
| 6,872,200 B2 | 3/2005 | Mann et al. | |
| 6,873,268 B2 | 3/2005 | Lebel et al. | |
| 6,878,132 B2 | 4/2005 | Kipfer | |
| 6,893,415 B2 | 5/2005 | Madsen et al. | |
| 6,899,695 B2 | 5/2005 | Herrera | |
| 6,899,699 B2 | 5/2005 | Enggaard | |
| 6,922,590 B1 | 7/2005 | Whitehurst | |
| 6,936,006 B2 | 8/2005 | Sabra | |

| | | |
|---|---|---|
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe |
| 2001/0041869 A1 | 11/2001 | Causey, III et al. |
| 2001/0056262 A1 | 12/2001 | Cabiri |
| 2002/0004651 A1 | 1/2002 | Ljunggreen et al. |
| 2002/0007154 A1 | 1/2002 | Hansen et al. |
| 2002/0016568 A1 | 2/2002 | Lebel |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0156462 A1 | 10/2002 | Stultz |
| 2003/0055380 A1 | 3/2003 | Flaherty |
| 2003/0065308 A1 | 4/2003 | Lebel et al. |
| 2003/0088238 A1* | 5/2003 | Poulsen et al. ............ 604/890.1 |
| 2003/0198558 A1 | 10/2003 | Nason et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0204744 A1 | 10/2004 | Penner et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0113745 A1 | 5/2005 | Stultz |
| 2005/0124866 A1 | 6/2005 | Elaz et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0088271 A1 | 4/2007 | Richards |
| 2007/0093750 A1* | 4/2007 | Jan et al. ................ 604/131 |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0009824 A1* | 1/2008 | Moberg et al. ............ 604/500 |
| 2008/0208627 A1 | 8/2008 | Skyggebjerg |

FOREIGN PATENT DOCUMENTS

| | | |
|---|---|---|
| DE | 196 27 619 A | 1/1998 |
| DE | 102 36 669 A | 2/2004 |
| EP | 0 062 974 | 10/1982 |
| EP | 0 496 141 | 7/1992 |
| EP | 0 612 004 | 8/1994 |
| EP | 0 580 723 | 10/1995 |
| EP | 0 275 213 | 7/1998 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/04301 | 2/1998 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/068015 | 9/2002 |
| WO | WO 02/084336 | 10/2002 |
| WO | WO 02/100469 | 12/2002 |
| WO | WO 03/026726 | 4/2003 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/067217 | 6/2006 |
| WO | WO 2006/097453 | 9/2006 |
| WO | WO 2006/105792 | 10/2006 |
| WO | WO 2006/105793 | 10/2006 |
| WO | WO 2006/105794 | 10/2006 |

WO WO 2007/141786 12/2007

OTHER PUBLICATIONS

Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

The Medtronic Diabetes Connection, 2006, 6 pages.

OmniPod Insulin Management System-Investor Relations- Press Release, Feb. 1, 2005, http://investors.insulet.com/phoenix.zhtml?c=209336&p=irol-newsArticle&ID=988708&highlight=1 page.

OmniPod Quick Start Guide, 2007, 2 pages.

Patent Abstracts of Japan, vol. 1999, No. 04, and JP 11 010036, Apr. 30, 1999 and Jan. 19, 1999, Toray Ind. Inc.

U.S. Appl. No. 11/362,616.

Medtronic News Release, "Medtronic Receives FDA Approval for World's First Insulin Pump with Real-time Continuous Glucose Monitoring," Apr. 13, 2006, 3 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

* cited by examiner

OPERATING AN INFUSION PUMP SYSTEM

CROSS-REFERENCE TO RELATED APPLICATIONS

This application is a continuation of U.S. patent application Ser. No. 11/522,603 filed on Sep. 18, 2006 by Mark Estes et al., which claims priority to: (1) U.S. Provisional Application Ser. No. 60/720,411 filed on Sep. 26, 2005 by Mernoe et al. and entitled "Precision Drive Mechanism," (2) U.S. Provisional Application Ser. No. 60/720,405 filed on Sep. 26, 2005 by Mernoe et al. and entitled "Flexible Pushrod Mechanism," and (3) U.S. Provisional Application Ser. No. 60/721,267 filed on Sep. 28, 2005 by Estes et al. and entitled "Infusion Pump with Removable Controller." The contents of these earlier applications are fully incorporated by reference herein.

TECHNICAL FIELD

This document relates to an infusion pump system, such as a medical infusion pump system.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

A number of factors may affect the design of infusion pump devices. One such factor is the size of the device. The pump device may be sized to house the various pump components, yet a large device may reduce the portability for the user. Another factor that may affect the design of an infusion pump device is the convenience to the user. For example, if the pump device is designed to be controlled via a user interface on a large wireless module that must be separately carried, the user may not be able to monitor the operation of the infusion pump during use without first locating, handling, and interfacing with the separate wireless module. A number of infusion pump components can impact the overall size and portability of an infusion pump system and the convenience to the user.

SUMMARY

Some embodiments of a medical infusion pump system include a pump device and a removable controller device. When the pump device and the removable controller device are removably attached to one another, the components may provide a portable infusion pump unit to dispense medicine to a user. In particular embodiments, the removable controller device includes a user interface to readily provide information, for example, about the operation of the pump.

In some embodiments, a medical infusion pump system may include a pump device having a drive system to dispense a medicine from the pump device. At least a portion of the drive system may be in electrical communication with one or more electrical contacts of the pump device. The system may also include a removable controller device having a user interface. The removable controller device may be removably attachable to the pump device in a fixed relationship. The controller device may include one or more electrical contacts that engage the electrical contacts of the pump device when removably attached.

Particular embodiments of a medical infusion pump system may include a pump device having a drive system to dispense a medicine from the pump device. The system may also include a first removable controller device having a first user interface. The first removable controller device may be mechanically attachable to the pump device and may be electrically connected to the pump device when mechanically attached. The system may further include a second removable controller device having a second user interface that is different from the first user interface. The second removable controller device may be mechanically attachable to the pump device and may electrically connected to the pump device when mechanically attached. In certain aspects, the pump device may be mechanically attachable to only one of the first and second removable controller devices at a time.

Some embodiments of a medical infusion pump system may include a pump device having a drive system to dispense a medicine from the pump device. The pump device may include a first battery. The system may also include a removable controller device mechanically attachable to the pump device. The removable controller device may be electrically connected to the pump device when mechanically attached. The controller device may include a second battery. The first battery may have a greater energy density than the second battery and may provide energy to charge the second battery over a period of time. The second battery may provide energy to at least a portion of the drive system of the pump device.

In certain embodiments, a medical infusion pump system includes a pump device and a removable controller device. The pump device may include a pump housing that defines a space to receive a medicine and a drive system to dispense the medicine when received by the pump housing. The drive system may include a piston rod that is incrementally movable to apply a dispensing force. The pump device may also include one or more electrical contacts disposed on the pump housing. At least a portion of the drive system may be in electrical communication with the one or more of the electrical contacts. The removable controller device may include a controller housing that is removably attachable to the pump housing in a fixed relationship. The removable controller device may also include one or more electrical contacts disposed on the controller housing. The electrical contacts of the controller device may be engageable with the electrical contacts of the pump device when removably attached. The removable controller device may further include a user interface arranged on the controller housing. The user interface may include a display and one or more user-selectable buttons. The pump device and the controller device, when removably attached, may provide a hand-graspable portable unit.

Some embodiments described herein may include a method for operating a medical infusion pump system. The method may include transmitting electrical energy, from a first battery in a pump device to a second battery in a removable controller device. The pump device may include a drive system to dispense a medicine from the pump device, and the removable controller device may be removably attached to and electrically connected to the pump device. The method may also include intermittently transmitting electrical energy from the second battery in the removable controller device to at least a portion of the drive system of the pump device. The first battery may have a greater energy density than the second battery and may provide energy to charge the second battery over a period of time.

These and other embodiments may provide one or more of the following advantages. First, the infusion pump system may be portable so that a user can wear the pump device (e.g., adhered to the user's skin or carried in a user's pocket or portion of clothing) and receive the infused medicine throughout the day or night. Second, the pump device of the infusion pump system may include a drive system that controllably dispenses medicine in a reliable manner. Third, the pump device of the infusion pump system can be removably attached to a controller device having a user interface. As such, the user can readily monitor the operation of the pump device without the need for carrying and operating an separate wireless module. Fourth, the infusion pump system may comprise two or more removable controller devices having different user interfaces. In these circumstances, a first controller device having a first user interface can be selected for use with the pump device, or a second controller device having a second user interface can be selected for use with the pump device. Fifth, the pump device may be capable of dispensing a first medicine when connected with a first controller device and may be capable of dispensing a second medicine when connected with a second controller device. Sixth, the pump device may include a first battery that recharges a second battery in the controller device, which in turn provides power to the drive system of the pump. Thus, each time a new pump device is connected to the controller device, the second battery in the reusable controller device is recharged, thereby reducing or possibly eliminating the need for separate recharging of the controller device.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
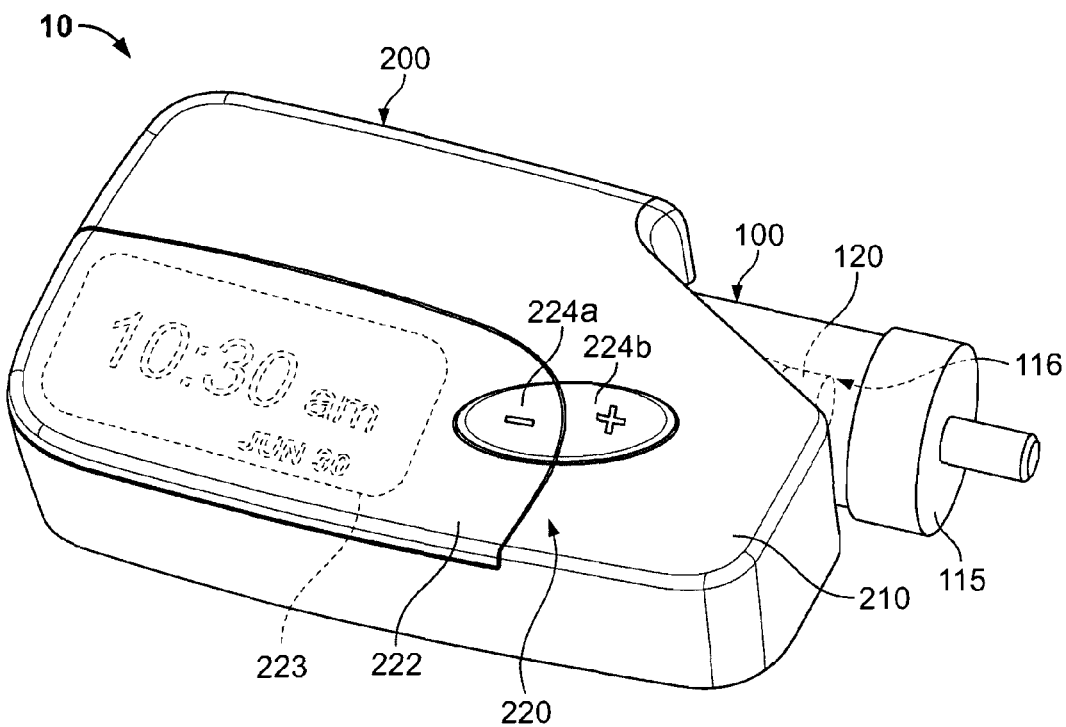
FIG. 1 is a perspective view of an infusion pump system, in accordance with some embodiments.
Figure 2:
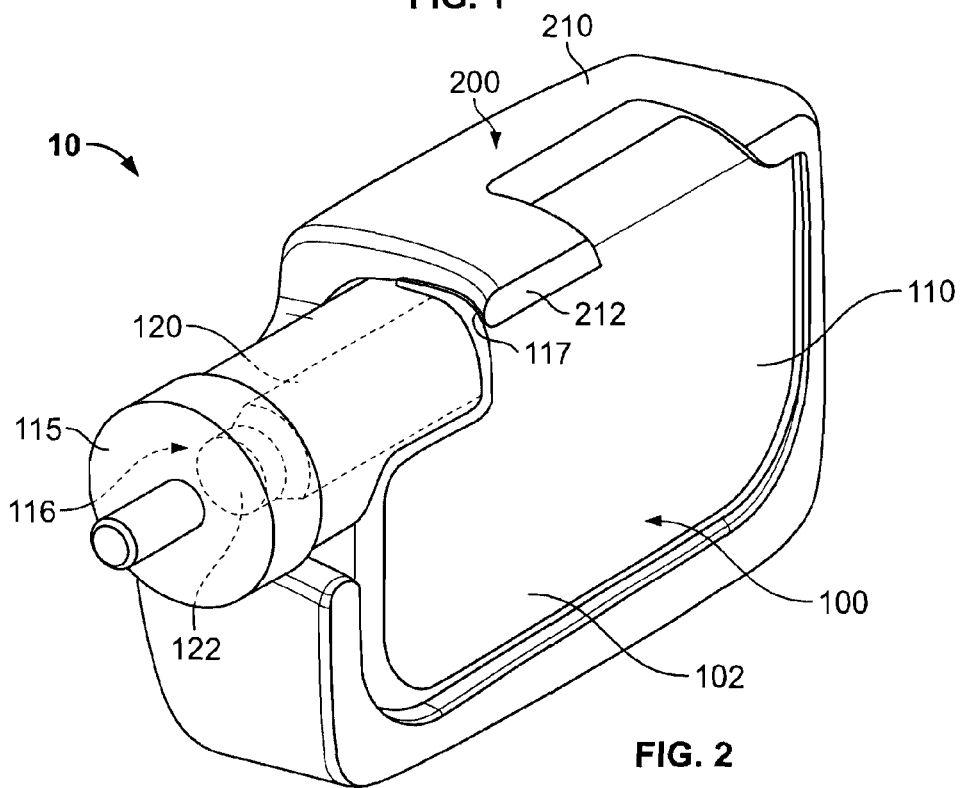
FIG. 2 is another perspective view of the infusion pump system of FIG. 1.

Referring to FIGS. 1-2, some embodiments of an infusion pump system 10 include a pump device 100 that can communicate with a controller device 200. The pump device 100 includes a housing structure 110 that defines a cavity 116 in which a fluid cartridge 120 is received. In this embodiment, the pump system 10 in a medical infusion pump system that is configured to controllably dispense a medicine from the cartridge 120. As such, the fluid cartridge 120 may contain a medicine to be infused into the tissue or vasculature of a targeted individual, such as a human or animal patient. For example, the pump device 100 can be adapted to receive a medicine cartridge 120 in the form of carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines.

In some embodiments, the controller device 200 may be removably attached to pump device 100 so that the two components are mechanically mounted to one another in a fixed relationship. Such a mechanical mounting can releasably secure an electrical connection between the removable controller device 200 and the pump device 100. For example, the controller device 200 may be in electrical communication with a portion of a drive system (not shown in FIGS. 1-2) of the pump device 100. As described in more detail below, the pump device 100 includes a drive system that causes controlled dispensation of the medicine or other fluid from the cartridge 120. In some embodiments, the drive system incrementally advances a piston rod (not shown in FIGS. 1-2) longitudinally into the cartridge 120 so that the fluid is force out of the output end 122. In this embodiment, the septum at the output end 122 can be pierced to permit fluid outflow when a cap member 115 is connected to the pump housing structure 110 (described in more detail below, for example, in connection with FIG. 5). Thus, when the pump device 100 and the controller device 200 are removably attached and thereby electrically connected, the controller device 200 communicates electronic control signals via hard-wire-connection to the drive system or other components of the pump device 100. In response to the electrical control signals from the controller device 200, the drive system of the pump device 100 causes medicine to incrementally dispense from the medicine cartridge 120.

Still referring to FIGS. 1-2, The controller device 200 can include a controller housing structure 210 that is configured to mate with a complementary portion of the pump housing structure 110 so as to form a releasable mechanical connection. For example, the controller housing structure 210 may define a cavity (refer, for example, to FIG. 6) that mates with a portion of the pump housing structure 110 for a snap fit engagement. Also, the controller housing structure 210 may include a finger 212 that engages a mating surface 117 of the pump housing structure 110 when the controller device 200 is removably attached to the pump device 100. As described in more detail below in connection with FIGS. 5-6, a magnetic attachment may be employed to releasably secure the pump device 100. For example, the magnetic attachment can serve to retain the pump housing structure 110 in the cavity defined by the controller housing structure 210. In alternative embodiments, one or more releasable connector devices (e.g., mating tongues and grooves, mounting protrusions friction fit into mating cavities, or the like) can be used to further implement the releasable securement of the controller device 200 to the pump device 100.

As described in more detail below in connection with FIGS. 5-6, the pump device 100 may include one or more electrical contacts (e.g., conductive pads, pins, and the like) that are exposed to the controller device 200 and that mate with complementary electrical contacts on the adjacent face of the controller device 200. The electrical contacts provide the electrical communication between the control circuitry of the controller device 200 and at least a portion of the drive system or other components of the pump device 100. For example, in some embodiments, the electrical contacts permit the transmission of electrical control signals to the pump device 100 and the reception of feedback signals (e.g., sensor signals) from particular components within the pump device 100.

Still referring to FIGS. 1-2, the controller device 200 includes a user interface 220 that permits a user to monitor the operation of the pump device 100. In some embodiments, the user interface includes a display 222 and one or more user-selectable buttons (e.g., two buttons 224a and 224b in this embodiment). The display 222 may include an active area 223 in which numerals, text, symbols, images, or combination thereof can be displayed. For example, the display 222 may be used to communicate a number of settings or menu options for the infusion pump system 10. In this embodiment, the user may press one or more of the buttons 224a and 224b to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As described in more detail below, in some embodiments, the user can adjust the settings or otherwise program the controller device 200 by pressing one or more buttons 224a and 224b of the user interface 220. In embodiments of the infusion pump system 10 configured to dispense insulin, the user may press one or more of the buttons 224a and 224b to change the dispensation rate of insulin or to request that a bolus of insulin be dispensed immediately or at a scheduled, later time.

As shown in FIG. 1, the display 222 of the user interface 220 may be configured to display quick reference information when no buttons 24a and 224b have been pressed. In this example, the active area 223 of the display 222 can display the time and the date for a period of time after no button 224a or 224b has been actuated (e.g., five seconds, 10 seconds, 30 seconds, 1 minute, 5 minutes, or the like). Thereafter, the display 222 may enter sleep mode in which the active area 223 is blank, thereby conserving battery power. In addition or in the alternative, the active area can display particular device settings, such as the current dispensation rate or the total medicine dispensed, for a period of time after no button 224a or 224b has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a or 224b has been actuated (e.g., after 15 seconds or the like), and then the display 22 can enter sleep mode and become blank after a second period of time in which no button 224a or 224b has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the user interface 220 connected to the pump device 100. Such monitoring capabilities may provide comfort to a user who may have urgent questions about the current operation of the pump device 100 (e.g., the user may be unable to receive immediate answers if wearing an infusion pump device having no user interface attached thereto).

Also, there is no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 removably attached to the pump device 100, without the requirement of locating and operating a separate monitoring module.

It should be understood from the description herein that the user interface 200 is not limited to the display and buttons depicted in FIG. 1. For example, in some embodiments, the user interface 220 may include only one button or may include a greater numbers of buttons, such as three buttons, four buttons, five buttons, or more. In another example, the user interface of the controller device 200 may include touch screen so that a user may select buttons defined by the active area of the touch screen display. Alternatively, the user interface may comprise audio inputs or outputs so that a user can monitor the operation of the pump device. Previously incorporated U.S. Provisional Application Ser. No. 60/721,267 also describes a number of configurations for a removable controller device and a user interface for the device in addition to the configuration illustrated in FIGS. 1-2 herein.

Figure 3:
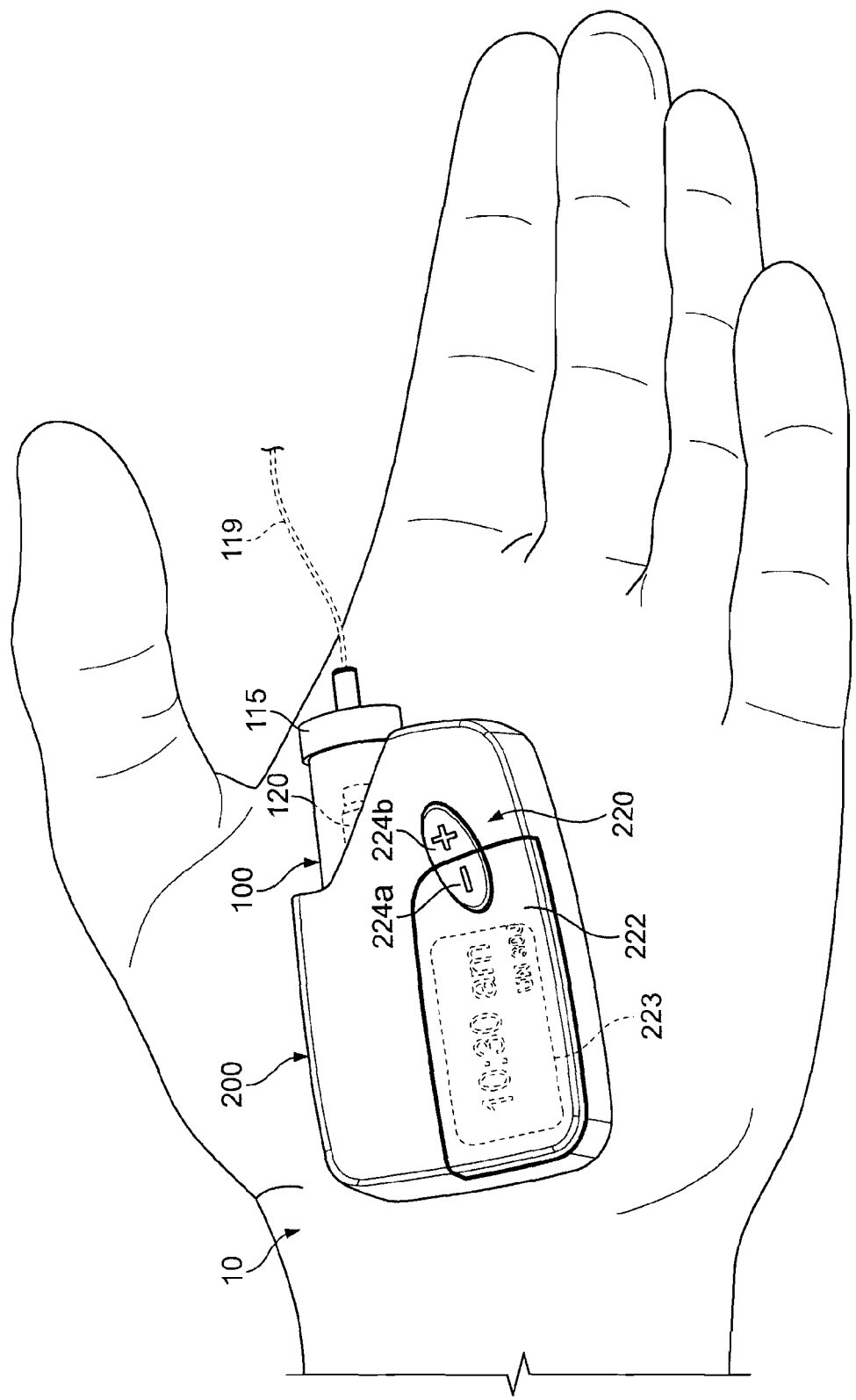
FIG. 3 is another perspective view of the infusion pump system of FIG. 1.

Referring to FIG. 3, the infusion pump system 10 may be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. As described in more detail below, the drive system may be housed in the housing structure 110 of the pump device 100 in a compact manner so that the pump device 100 has a reduced length. For example, in the circumstances in which the medicine cartridge 120 has a length of about 6 cm to about 7 cm (about 6.4 cm in this embodiment), the overall length of the pump housing structure 110 (which contains medicine cartridge and the drive system) can be about 7 cm to about 9 cm (about 8.3 cm or less in this embodiment).

In addition, the pump housing structure 110 may have an overall height of about 1.5 cm to about 4 cm (about 2.9 cm or less in this embodiment) and an overall thickness of about 8 mm to about 20 mm (about 14.5 mm or less in this embodiment). In such circumstances, the controller device 200 can be figured to mate with the compact pump housing 110 so that, when removably attached to one another, the components define a portable infusion pump unit that stores a relatively large quantity of medicine compared to the overall size of the unit. For example, in this embodiment, the infusion pump system 10 (including the pump device 100 attached to the removable controller device 200) may have an overall length of about 7 cm to about 9 cm (about 8.5 cm or less in this embodiment), an overall height of about 1.5 cm to about 4 cm (about 3.5 cm or less in this embodiment), and an overall thickness of about 8 mm to about 20 mm (about 15 mm or less in this embodiment).

As shown in FIG. 3, this embodiment of the infusion pump system 10 is pocket-sized so that the pump device 100 and controller device 200 can be worn in the user's pocket or in another portion of the user's clothing. In such embodiments, the cap member 115 of the pump device 100 may be configured to connect with a flexible tube 119 of an infusion set. The infusion set may include the tube 119 that extends toward a skin adhesive patch and connects with an infusion cannula (not shown in FIG. 3). The skin adhesive patch can retain the infusion cannula in fluid communication with the tissue or vasculature of the patient so that the medicine dispensed through the tube 119 passes through the cannula and into the user's body. As described below in connection with FIG. 5, the cap member 115 may provide fluid communication between the output end 122 (FIG. 1) of the medicine cartridge 120 and the tube 119 of the infusion set. In these embodiments, the user can carry the portable infusion pump system 10 (e.g., in the user's pocket, connected to a belt clip, or adhered to the user's skin) while the tube 119 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

In other embodiments, the infusion pump system 10 may be configured to adhere to the user's skin directly at the location in which the skin is penetrated for medicine infusion. For example, a rear surface 102 of the pump device 100 (refer, for example, to FIG. 2) may include a skin adhesive patch so that the pump device 100 is physically adhered to the skin of the user at a particular location. In these embodiments, the cap member 115 may have a configuration in which medicine passes directly from the cap member 115 into an infusion cannula that is penetrated into the user's skin. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 220 that is removably attached thereto.

Figure 4:
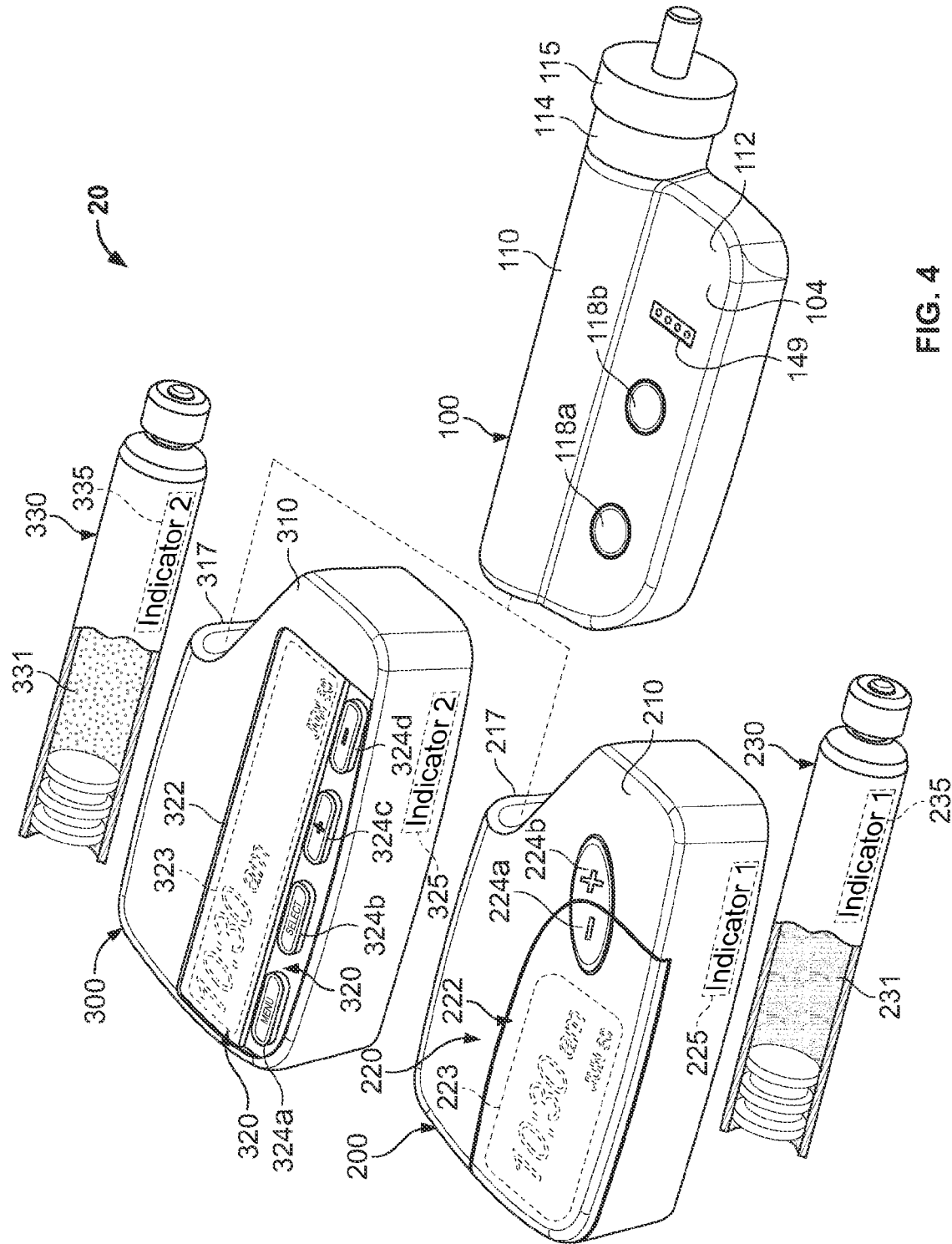
FIG. 4 is a perspective view of an infusion pump system, in accordance with some embodiments.

Referring to FIG. 4, some embodiments of an infusion pump system 20 may include a pump device 100 that is configured to mate with any one of two or more controller devices (e.g., controller device 200 and controller device 300 in this embodiment) that are different from one another. The controller devices 200 and 300 may have different user interfaces 220 and 320, respectively, so as to provide different control options to the user. For example, some users may select the first controller device 200 for use in combination with the pump device 100 for a simplified input comprising two buttons 224a and 224b in the user interface 220. In another example, some users may select the second controller device 300 for use in combination with the pump device 100 for a larger size display 322 and increased button options (e.g., four buttons 324a, 324b, 324c, and 324d) in the user interface 320.

The pump device 100 can be releasably secured to any one of the controller devices 200 and 300 in the infusion pump system 10. As previously described, the pump device 100 includes a pump housing structure 110, and at least a portion of the pump housing structure 110 is configured to be received in a complementary cavity 215 or 315 (FIGS. 8-10) defined in the controller housing structure 210 or 310. When the pump device 100 is received by the controller device 200 or 300, a retainer finger 217 or 317, respectively, may engage a mating surface of the pump housing structure 110. In addition, a magnetic attachment can be used to releasably secure the pump device 100 to any of the controller housing structures 210 and 310. In such circumstances, the pump device 100 includes one or more magnetically attractable devices 118a and 118b (e.g., permanent magnets in this embodiment) exhibited on the front surface 104 of the pump housing structure 110 which magnetically engage complementary devices (refer, for example to FIG. 8) arranged on the controller housing structure 210 or 310. As such, when the pump device 100 is received in the cavity defined by the controller housing structure 210, the magnetically attractable devices 118a and 118b form a magnetic attachment to retain the pump device 100 therein. Also as described in more detail below, the pump device 100 may include one or more electrical contacts 149 arranged to engage complementary electrical contacts 249 (refer, for example to FIG. 8) arranged on the controller housing structure 210 or 310.

In some embodiments of the infusion pump system 20, the first and second controller devices 200 and 300 may be configured to control the dispensation of the same type of medicine when the pump device 100 is removably attached thereto. For example, a medicine cartridge containing insulin may be received in the pump device 100, and the user may select (e.g., based upon the user's preference, based upon an expert's recommendation, or a combination thereof) either the first controller device 200 or the second controller device 300 for attachment to the pump device 100. Because the first controller device 200 includes a user interface 220 that is different from the user interface 320 of the second controller device 300, the user may prefer the operation, appearance, or functionality of one controller device (200 or 300) over the other (300 or 200). For example, some users may select the first controller device 200 to provide a simplified input comprising two buttons 224a and 224b in the user interface 220 (e.g., lower complexity of input options may be preferable to child users). In another example, some users may select the second controller device 300 to provide a larger size display 322 and increased button options 324a, 324b, 324c, and 324d in the user interface 320 (e.g., increased input options may be preferably to users who frequently monitor a number of pump settings and summary screens). Alternatively, the controller devices 200 and 300 may include the same user interface option, but may have different appearances so as to provide the user with a variety of styles. For example, the controller device 200 may have a different outer shape or a different color than that of the second controller device 300, thereby permitting the user to select one of the controller devices 200 or 300 depending upon the desired appearance of the infusion pump system 20.

Still referring to FIG. 4, in some embodiments of the infusion pump system 20, the first and second controller devices 200 and 300 may be configured to control the dispensation of the different types of medicine when the pump device 100 is removably attached thereto. For example, a first medicine cartridge 230 containing a first type of medicine 231 can be received in the pump device 100. In these circumstances, the first controller device 200 may be removably attached to the pump device 100 (having the first medicine container 230 received therein) so as to control the dispensation of the first type of medicine 231. In another example, a second medicine cartridge 330 containing a second type of medicine 331 can be received in the pump device 100. Here, the second controller device 300 may be removably attached to the pump device 100 (having the second medicine container 330 received therein) so as to control the dispensation of the second type of medicine 331. Accordingly, the infusion pump system 20 can employ a single pump device 100 that is capable of dispensing any one of two or more medicines (e.g., medicines 231 and 331 in this embodiment) when connected to any one of two or more controller devices (e.g., controller devices 200 and 330, respectively, in this embodiment).

Such embodiments of the infusion pump device 20 permit a user to transition from the infusion of one type of medicine to a second type of medicine without learning to operate a new type of pump device. In one embodiment, the pump device 100 may be used in combination with the first controller device 200 so as to deliver a medicine 231 for the treatment of Type 2 Diabetes. Examples of such medicines 231 include Exenatide, which is commercially available under the name BYETTA™, or others in a class of medicines for Type 2 Diabetes called incretin mimetics. These medicines may improve control of Type 2 Diabetes by aiding the user's pancreas produce an appropriate amount of insulin. As described in more detail below in connection with FIGS. 5A-D, the second controller device 200 may include a user interface 220 configured to provide information and monitoring options for the infusion of Exenatide.

If the user's Diabetes progresses over time to become Type 1 Diabetes, the user may continue to use the same type of pump device 100 but with a different controller device 300 (e.g., a controller device for use in the infusion of insulin or other medicines to treat Type 1 Diabetes). Thus, the user is not required to obtain and learn about a new type of pump device 100. Instead, the user may conveniently attach the same type of pump device 100 (this time including a cartridge 330 with insulin 331) to a second controller device 300. As described in more detail below in connection with FIGS. 6A-D, the second controller device 300 may include a user interface 320 configured to provide information and monitoring options for the infusion of insulin. In some circumstances, the dispensation rate, dosage amount, and other parameters of insulin infusion may be different from other infused medicines (e.g., Exenatide), so the user interface 320 may provide different monitoring options or different textual information compared to the user interface 220 of the first controller device 200.

Moreover, such embodiments of the infusion pump system 20 may provide manufacturing benefits. For example, the manufacturer may not be required to manufacture a different type of pump device 100 for each of the different types of controllers. Instead, the pump device 100 can be mass produced in high quantities for use in conjunction with any one of a plurality of controller devices (e.g., controller devices 200 and 300 in this embodiment).

Optionally, the first controller device 200 may include an indicia 225 that identifies the particular type of medicine cartridge 230 or medicine 231 with which it is to be employed. The medicine cartridge 230 may include a similar indicia 235. As such, the user can verify that the appropriate type of medicine 231 is received in the pump device 100 for controlled dispensation by the controller device 200. For example, the indicia 225 may include a label, marking, etching, or the like disposed on the controller housing structure 210 that indicates a particular name, code, or other identifier corresponding to a particular medicine 231 (e.g., "EXENATIDE" or "BYETTA" or another identifier). The indicia 235 disposed on the medicine cartridge 230 may include a similar label, marking, etching, or the like disposed on an outer surface of the cartridge 230 so as to indicate a particular name, code, or other identifier corresponding to the particular medicine 231. The second controller device 300 may also include an indicia 325 that identifies the particular type of medicine cartridge 330 or medicine 331 with which it is to be employed (e.g., "INSULIN" or another identifier). The indicia 325 may match a corresponding indicia 335 arranged on the medicine cartridge 330. Thus, a person or machine will be able to interpret the indicia 235 on the first cartridge 230 and the indicia 225 on the first controller device 220 to know that the first cartridge 230 is used in conjunction with the first controller device 200. Similarly, a person or machine will be able to interpret the indicia 335 on the second cartridge 230 and the indicia 325 on the second controller device 320 to know that the second cartridge 330 is used in conjunction with the second controller device 300.

Figure 5B:
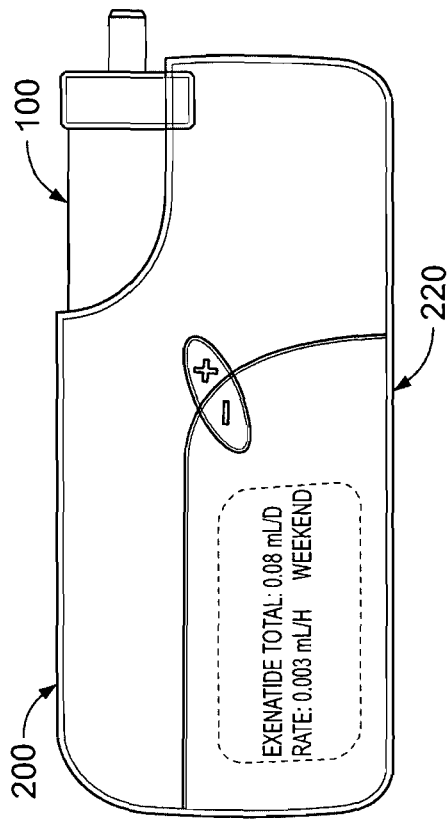
FIGS. 5A-D are examples of a user interface of a first controller device in the infusion pump system of FIG. 4.
Figure 5D:
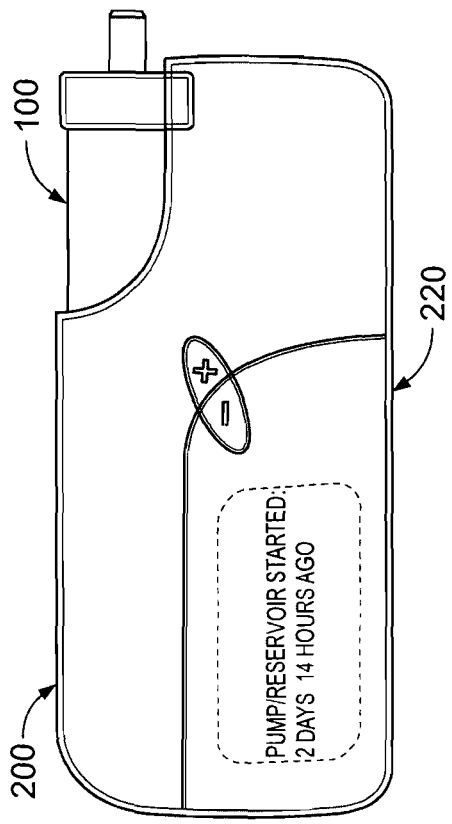
Figure 5A:
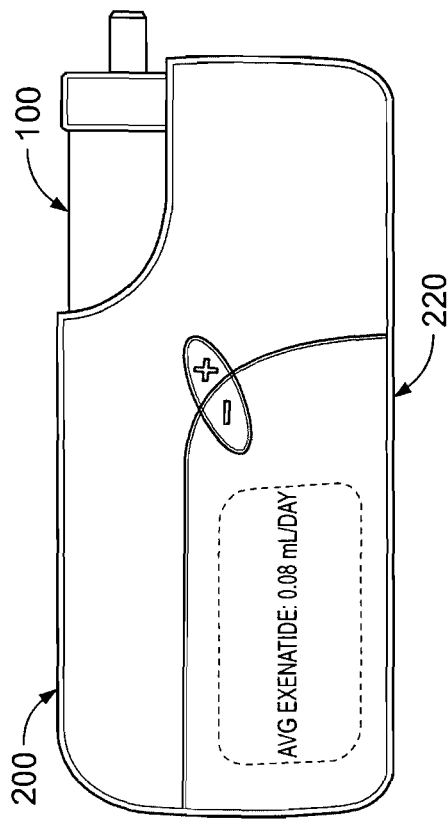
Figure 5C:
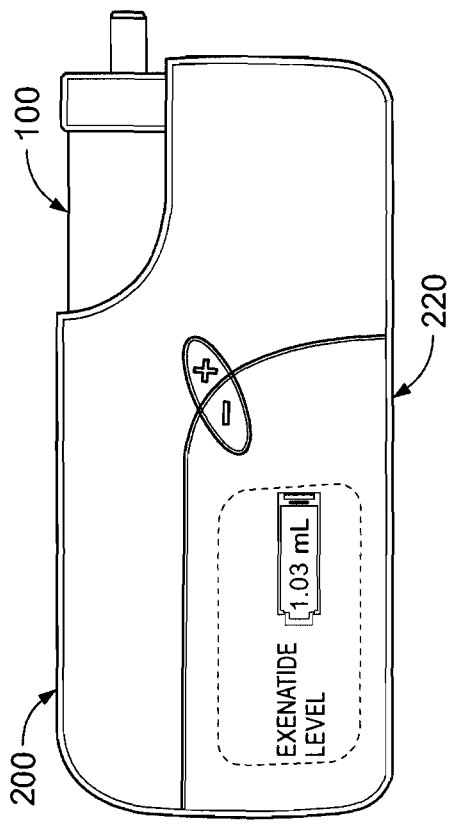

Referring to FIGS. 5A-D, in some embodiments, the user interface 220 of the first controller device 200 may be configured to provide information and monitoring options for the infusion of a first type of medicine, such as Exenatide. In this embodiment, the user interface 220 comprises a display and two buttons as previously described in connection with FIGS. 1-4. The user may press one or more buttons of the user interface 220 to toggle through a number of monitoring screens that provide information regarding the dispensation of the Exenatide medicine or regarding the operation of the pump device. For example, as shown in FIGS. 5A-D, the user interface 220 may provide information regarding the average amount of Exenatide infused per day (FIG. 5A), regarding the total amount of Exenatide infused on the current day and the average dispensation rate of the pump device on the current day (FIG. 5B), regarding the amount of Exenatide remaining in the medicine cartridge received in the pump device 100 (FIG. 5C), and regarding the amount of time since the pump device 100 started dispensing Exenatide (FIG. 5D). In some circumstances, the user may be able to press one or more buttons of the user interface 220 (e.g., press both buttons at the same time, press and hold one button for a period of time, or the like) so as to adjust particular settings of the infusion pump system. For example, the user may press and hold both buttons when a particular screen is displayed so as to adjust the dispensation rate, to adjust the time or date, or to reset the average dispensation calculation.

Figure 6B:
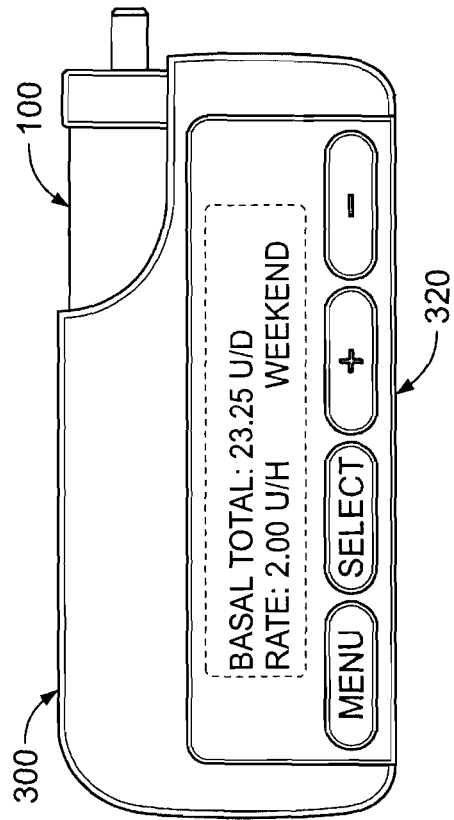
FIGS. 6A-D are examples of a user interface of a second controller device in the infusion pump system of FIG. 4.
Figure 6D:
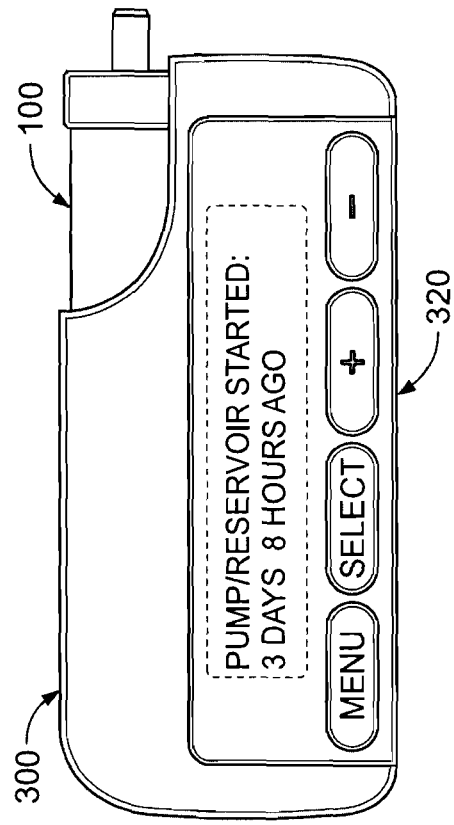
Figure 6A:
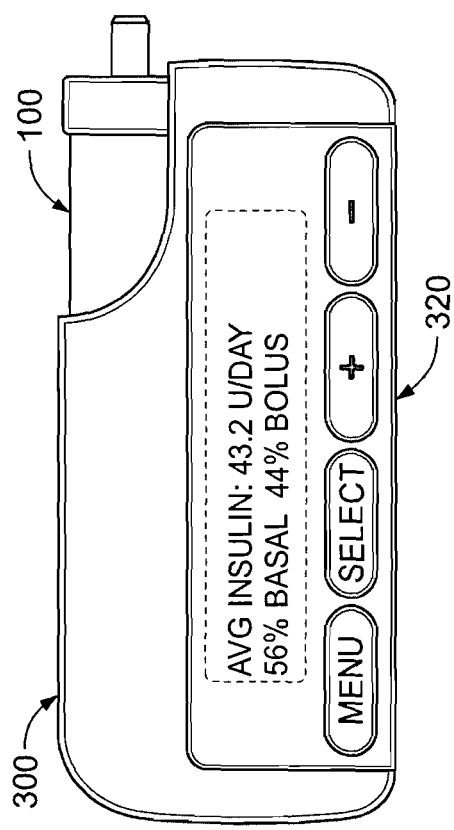
Figure 6C:
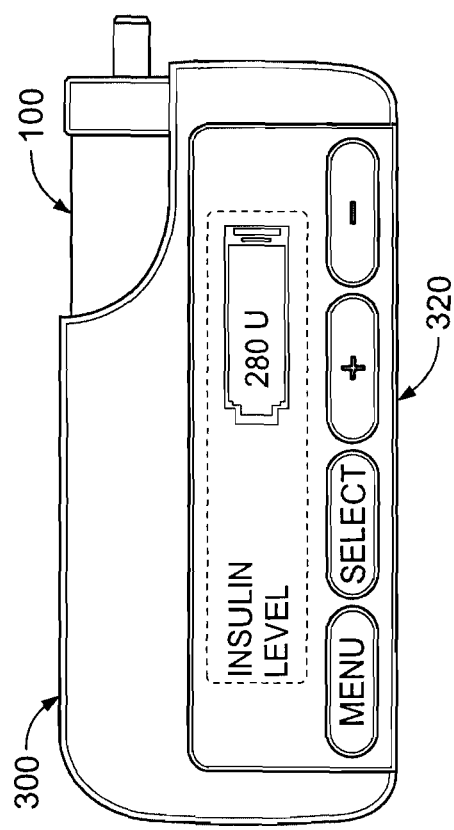

Referring to FIGS. 6A-D, in some embodiments, the user interface 320 of the second controller device 300 may be configured to provide information and monitoring options for the infusion of a second type of medicine, such as insulin. In this embodiment, the user interface 320 comprises a display and four buttons as previously described in connection with FIG. 4. The user may press one or more buttons of the user interface 320 to toggle through a number of monitoring screens that provide information regarding the dispensation of the insulin medicine or regarding the operation of the pump device 100. For example, as shown in FIGS. 6A-D, the user interface 320 may provide information regarding the average amount of insulin infused per day (FIG. 6A), regarding the total amount of insulin infused on the current day and the average dispensation rate of the pump device on the current day (FIG. 6B), regarding the amount of insulin remaining in the medicine cartridge received in the pump device 100 (FIG. 6C), and regarding the amount of time since the pump device 100 started dispensing insulin (FIG. 6D). In some circumstances, the user may be able to press the menu and select buttons button of the user interface 320 so as to toggle to a parameter adjustment screen, in which the "−" or "+" buttons may be used to adjust the values. For example, the user may adjust the dispensation rate, to adjust the time or date, or to reset the average dispensation calculation.

Figure 7:
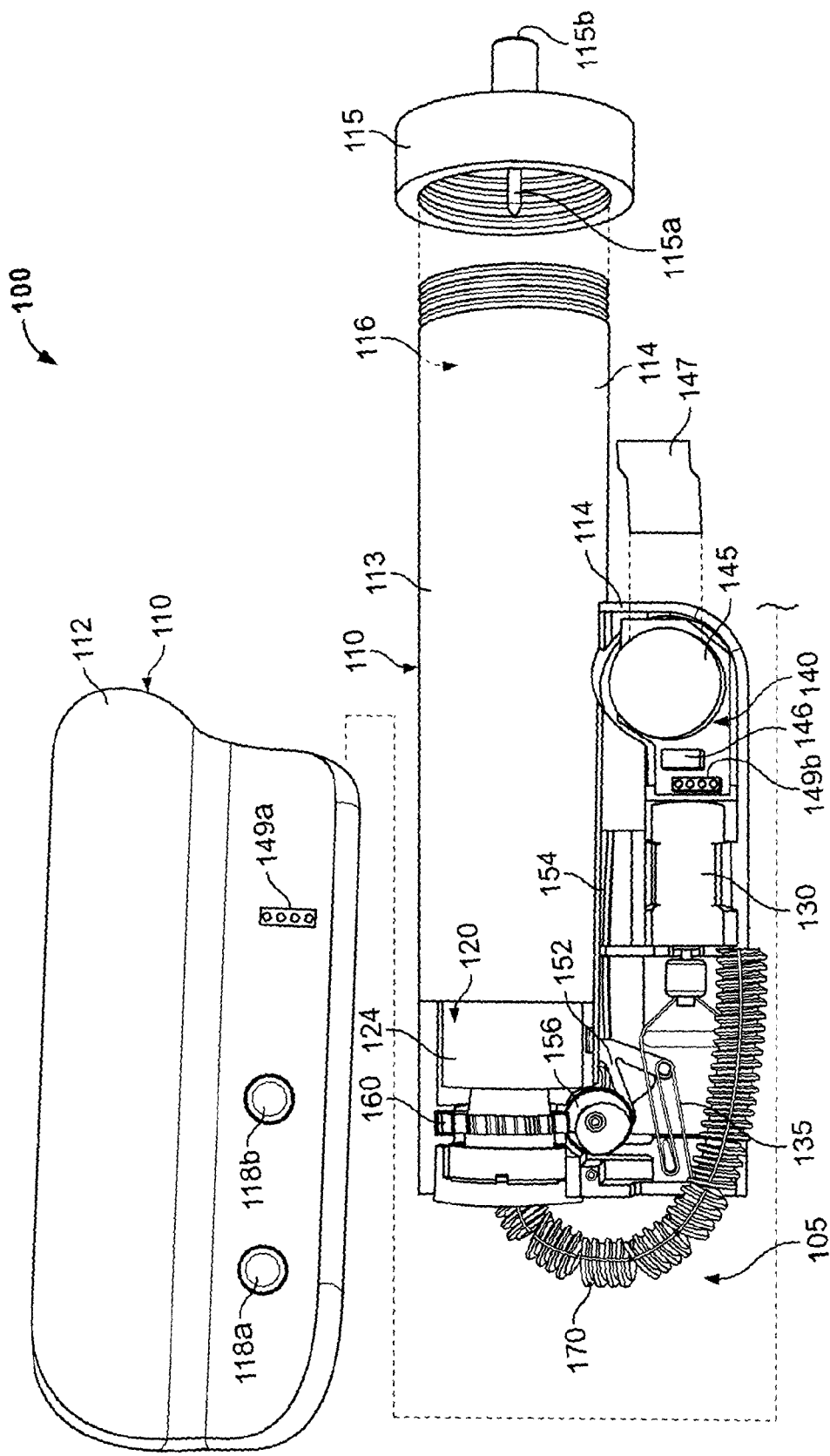
FIG. 7 is an exploded view of a pump device of the infusion pump system of FIG. 4.

Referring now to FIG. 7, the pump device 100 of the infusion pump system 10 or 20 may include a drive system 105 that is controlled by the removable controller device 200 or 300. Accordingly, the drive system 105 can accurately and incrementally dispense fluid from the pump device 100 in a controlled manner. In this embodiment, the pump housing structure 110 includes a detachable shell 112 that covers at least a portion of the drive system 105 and includes a frame portion 113 to which at least a portion of the drive system 105 is mounted. The detachable shell 112 may include an inner curved surface against which a curved section of a piston rod 170 rests. The detachable shell 112 can be part of the pump housing structure 110 that engages with the controller device 200 (or 300) as previously described in connection with FIGS. 1-4. As such, the detachable shell portion 112 may include the magnetically attractable devices 118a and 118b that releasably secure the pump device 100 to the controller device 200 (or 300). In addition, the detachable shell 112 may provide access to the electrical contacts 149a of the pump device 100. In this embodiment, the electrical contacts 149a are configured to align with the contact circuit device 149b arranged in the pump device 100. In other embodiments, the electrical contacts of the pump device 100 can be arranged directly on the contact circuit device 149b, and the detachable shell 112 may include a slot (in the location shown as numeral 149a) so as to permit electrical engagement with the controller device 200 (or 300).

One or both of the detachable shell 112 and the frame portion 114 can be molded from polymer material, such as Polycarbonate, Acrylonitrile Butadiene Styrene, or Acrylic. In this embodiment, the detachable shell portion 112 comprises a generally opaque, moldable material so that the drive system 105 and other components of the pump device are concealed from view. The frame portion 113 may include a cylindrical receiver 114 that defines the space 116 to receive the medicine cartridge 120 (FIG. 2). In some circumstances, at least a portion of the cylindrical receiver 114 is transparent or translucent so that the user may view the medicine cartridge 120 therein. Such a configuration provides the user with visual verification of when the medicine cartridge is empty or near empty (e.g., the plunger in the medicine cartridge has been fully advanced).

The receiver 114 may also include a connector to mate with the cap member 115. In this embodiment, the connector comprises an external thread pattern formed on the receiver 113 that mates with an internal thread pattern of the cap member 115. Accordingly, the cap member 115 can be secured to the frame portion 113 after the medicine cartridge 120 (FIG. 2) has been received therein. As shown in FIG. 7, the cap member may include a cartridge penetrator 115a that pierces the output end 122 (FIG. 2) of the medicine cartridge 120 when the cap member 115 is mounted to the frame portion 113. The cartridge penetrator 115a is in fluid communication with an tube connector 115b, which is connected to a tube 119 of an infusion set device (as previously described in connection with FIG. 3). As previously described, in some embodiments, the fluid cartridge 120 may occupy a majority of the length of the pump housing structure 110 (with the drive system 105 being arranged in a compact manner) so that the pump device 100 is wearable and portable.

Still referring to FIG. 7, some embodiments of the pump device 100 include a first battery 145 that is capable of transmitting electrical energy to the controller device 200 (or 300) when the pump device 100 is attached to the controller device 200 (or 300). Such energy transmission is described in more detail below in connection with FIG. 8. The first battery 145 may be arranged in a first circuit 140 that includes the contact circuit device 149b. The first circuit 140 may be simple and inexpensive so as to facilitate a low-cost pump device 100 that is disposable. The first circuit 140 may comprise a printed circuit board or a flexible circuit that is arranged in the frame portion 113 of the pump device 100. Optionally, the first circuit 140 may include a gateway circuit device 146 that permits the transmission of electrical energy from the first battery 145 to the controller device 200 (or 300). In some circumstances, the gateway circuit device 146 may be under the control of and directed by the control circuit in the controller device 200 (or 300). In some embodiments, the gateway circuit device 146 of the first circuit 140 may be in electrical communication (e.g., via one or more electrical wires or electrically conductive traces) with a force sensor 148 (refer to FIG. 11) arranged between the plunger connector 178 that the plunger 121. The force sensor 148 may comprise a force transducer or load cell that is capable of electrically communicating an applied force. As such, the force sensor 148 can provide feedback signals to the local pump circuit 140 (or to the control device 200 via the electrical contacts) so as to monitor the force transmitted to the plunger 121 of the medicine cartridge 120. Such information can be used, for example, to detect if an occlusion exists in the medicine flow path. Other sensors (e.g., a pressure sensor, a flow sensor, a rotation sensor, a displacement sensor, or the like) may be electrically connected to the first circuit 140 to provide feedback signals to the control device 200 via the electrical contacts. It should be understood that, in other embodiments, the first circuit 140 may be configured to operate without the gateway circuit device 146. For example, the control circuit in the removable controller device 200 may communicate via the electrical contacts directly with a portion of the drive system 105 (e.g., direct electrical communication with the motor 130), with one or more sensors disposed in the pump device 100 (e.g., with the force sensor 148), and with the first battery 145.

In this embodiment, the first battery 145 can be maintained in a storage mode and then switched to an activation mode when the pump device 100 used to dispense medicine. The storage mode can provide a long shelf life of storage life for the first battery 145. For example, when in storage mode, the first battery may retain a substantial portion of its charge for a period of more than six months, more than one year, or more than two years. As shown in FIG. 7, the first battery 145 may be equipped with a removable tab 147 that seals the first battery 145 to maintain it in the storage mode. Thus, when the pump device 100 is prepared for usage, the removable tab 147 can be pulled away from the first battery 145, which switches the first battery into the activation mode. When the first battery 145 is switched to the activation mode, the first battery 145 may dispense electrical energy for usage period in which the pump device is used. For example, in some embodiments, the first battery 145 may provide electrical energy to other components over a usage period of about one week to about one month, and about two weeks in this embodiment.

As shown in FIG. 7, some embodiments of the drive system 105 may include a rotational motor 130 that is coupled to a string member 135, which is used to adjust a ratchet mechanism 150. The operation of the drive system 105 is described in more detail below in connection with FIGS. 12A-C. The drive system 105 can provide a reliable and compact configuration for accurately dispensing the desired volume of fluid from the pump device 100. Moreover, the drive system 105 may comprise few, if any, high-cost actuator components or electronics, thereby facilitating the relatively low-cost production of a disposable and reliable pump device 100.

Figure 8:
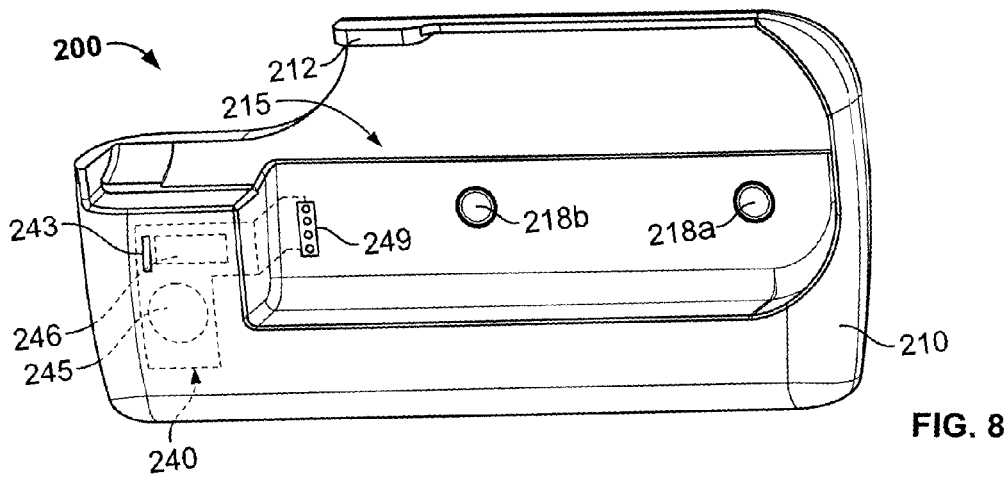
FIG. 8 is a perspective view of a controller device of the infusion pump system of FIG. 4.

Referring to FIG. 8, the controller device 200 can be attached to the pump device 100 in a removable manner. In this embodiment, the housing structure 210 of the controller device 200 defines a cavity 215 in which at least a portion of the pump device 100 can be received (refer, for example, to FIG. 2). When the pump device 100 is received in the cavity 215, the finger 212 of the controller housing structure 212 may engage a mating surface 117 (FIG. 2) of the pump device 100. In addition, the controller device 200 can include magnetically attractable devices 218a-b that align with the magnetically attractable devices 118a-b (FIG. 7) of the pump device 100. As such, the magnetically attractable devices 118a-b and 218a-b releasably secure the pump device 100 in the cavity 215 of the controller device 200. In some embodiments, both the devices 118a-b and 218a-b may comprise permanent magnets. In other embodiments, one set of the devices 118a-b or 218a-b may comprise permanent magnets while the opposing set of the devices 218a-b or 118a-b comprise a metallic material that is attractable to the permanent magnets.

The controller device 200 can also include one or more electrical contacts 249 that provide electrical communication to a controller circuit 240. In this embodiment, the electrical contacts 249 are arranged on the controller housing structure 210 so as to align with the electrical contacts 149a (or the electrical contact device 149b) of the pump device 100 (refer, for example, to FIG. 7). Accordingly, when the pump device 100 is removably attached to the controller device 200, the controller device 200 becomes electrically connected to the pump device 100 to provide for the communication of electrical control signals.

Still referring to FIG. 8, the controller circuit 240 of the controller device 200 may include a second battery 245 that can receive electrical energy from the first battery 145 (FIG. 7) disposed in the pump device 100. The hard-wired transmission of the electrical energy can occur through the electrical contacts 249 of the controller device 200. In such circumstances, the first battery 145 may include a high density battery that is capable providing a relatively large amount of electrical energy for its package size. Accordingly, the first battery 145 disposed in the pump device 100 can be used to deliver electrical energy over time (e.g., "trickle charge") to the second battery 245 when the controller device 200 is removably attached to the pump device 100. For example, the first battery 145 may comprise a zinc-air cell battery. The zinc-air cell battery 145 may have a large volumetric energy density compared to some other battery types. For example, the zinc-air cell battery 145 may have a volumetric energy density of greater than about 900 Watt-hours/Liter (Wh/L), about 1000 Wh/L to about 1700 Wh/L, and about 1200 Wh/L to about 1600 Wh/L. Also, the zinc-air cell battery may have long storage lives, especially in those embodiments in which the battery is sealed (e.g., by the removable tab 147 or the like) during storage and before activation. One exemplary a zinc-air cell battery is available from Duracell Corporation of Bethel, Conn., which provides a potential voltage of about 1.1V to about 1.6V (about 1.2V to about 1.4 V, and about 1.3 V in this embodiment), a current output of about 8 mA to about 12 mA (about 10 mA in this embodiment), and a storage capacity of greater than about 600 mA·h (about 650 mA·h in this embodiment).

The second battery 245 may include a high current output device that is capable discharging a brief current burst to power the drive system 105 of the pump device 100. Accordingly, the second battery 245 can be charged over a period of time by the first battery 145 and then intermittently deliver high-current bursts to the drive system 105 over a brief moment of time. For example, the second battery 245 may comprise a lithium polymer battery. The lithium polymer battery disposed in the controller device 200 may have an initial current output that is greater than the zinc-air cell battery disposed in the pump device 100, but zinc-air cell battery may have an energy density that is greater than the lithium polymer battery (e.g., the lithium polymer battery disposed in the controller device 200 may have a volumetric energy density of less than about 600 Wh/L). In addition, the lithium polymer battery is rechargeable, which permits the zinc-air battery disposed in the pump device 100 to provide electrical energy to the lithium polymer battery 245 for purposes of recharging. One exemplary lithium polymer battery is available from Sanyo Corporation of Japan, which provides a initial current output of about greater than 80 mA (about 90 mA to about 110 mA, and about 100 mA in this embodiment) and a maximum potential voltage of about 4.0V to and 4.4V (about 4.2 V in this embodiment). In other embodiments, it should be understood that the second battery 245 may comprise a capacitor device capable of recharging over time and intermittently discharging a current burst to activate the drive system 105.

Because the controller device 200 can be reusable with a number of pump devices 100 (e.g., attach a new pump device 100 after the previous pump device 100 is expended and disposed), the second battery 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second battery 245 in the "reusable" controller device 200, thereby reducing or possibly eliminating the need for separate recharging of the controller device 200 via a power cord plugged into a wall outlet.

The controller circuit 240 of the control device 200 includes a microcontroller device 246 that coordinates the electrical communication to and from the controller device 200. At least a portion of the controller circuit 240 can be embodied on a printed circuit board (or a flexible circuit substrate). The second battery 245 and the microcontroller 246 can be mounted to such a printed circuit board (or connect to such a flexible circuit substrate). Electrical connections from the electrical contacts 249 and the user interface 220 (FIG. 9) may extend along the printed circuit board to the microcontroller device 246. In this embodiment, the controller circuit 240 is disposed in a hollow space of the controller housing structure 210. For example, the controller housing structure can be formed from two molded portions that are welded or adhered to one another after the controller circuit 240 is assembled therein.

As shown in FIG. 8, some embodiments of the controller circuit 240 may include a cable connector 243 (e.g., a USB connection port or another data cable port). As such, a cable may be connected to the controller circuit 240 to upload data or program settings to the controller circuit or to download data from the controller circuit 240. For example, historical data of medicine delivery can be downloaded from the controller circuit 240 (via the cable connector 243) to a computer system of a physician or a user for purposes of analysis and program adjustments. Optionally, the data cable may also provide recharging power to the controller circuit 240.

Figure 9:
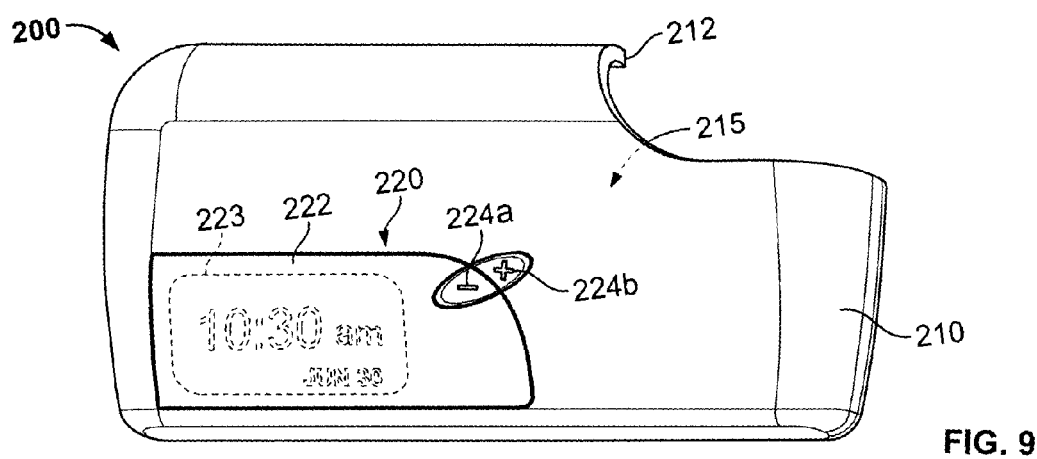
FIG. 9 is a perspective view of one controller device of the infusion pump system of FIG. 4.

Referring to FIG. 9, the user interface 220 of the controller device 200 can include input components, output components, or both that are electrically connected to the controller circuit 240 (FIG. 8). For example, in this embodiment, the user interface includes a display device 222 having an active area 223 that outputs information to a user and two buttons 224a and 224b that receive input from the user. Here, the display 222 may be used to communicate a number of settings or menu options for the infusion pump system 10. In this embodiment, the controller circuit 240 may receive the input commands from the user's button selection and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 100.

Figure 10:
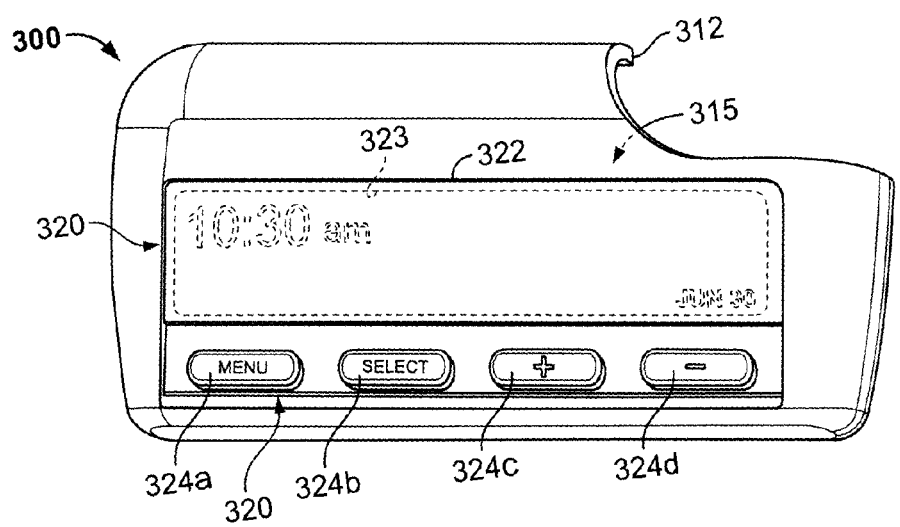
FIG. 10 is a perspective view of another controller device of the infusion pump system of FIG. 4.

Referring to FIGS. 9 and 10, the first controller device 200 has a user interface 220 that is different from the user interface 320 of the second controller device 300 so as to provide different control options. In the depicted embodiments, the first controller device 200 provides a simplified input comprising two buttons 224a and 224b in the user interface 220, and the second controller device 300 provides a larger size display 322 and increased button options (e.g., four buttons 324a, 324b, 324c, and 324d). As previously described, both controller devices 200 and 300 can be used to control the dispensation of medicine from the pump device 100. It should be understood from the description herein that the second controller device 300 can include a controller circuit that is similar to the controller circuit 240 (FIG. 8) of the first controller device 200. Accordingly, some embodiments of the second controller device 300 may include a second battery (to provide bursts of current to power the drive system 105 of the pump device 100), electrical contacts (to align with the contacts 149a or the contact device 149b of the pump device 100), and a microcontroller device. In addition, it should be understood from the description herein that the second controller device 300 can include a cavity 315 that is similarly shaped to the cavity 215 (FIG. 8) of the first controller device 200. Also, the second controller device 300 may include a finger 312, magnetically attractable devices, or both similar to the finger 212 and devices 218a-b depicted in FIG. 8.

Figure 11:
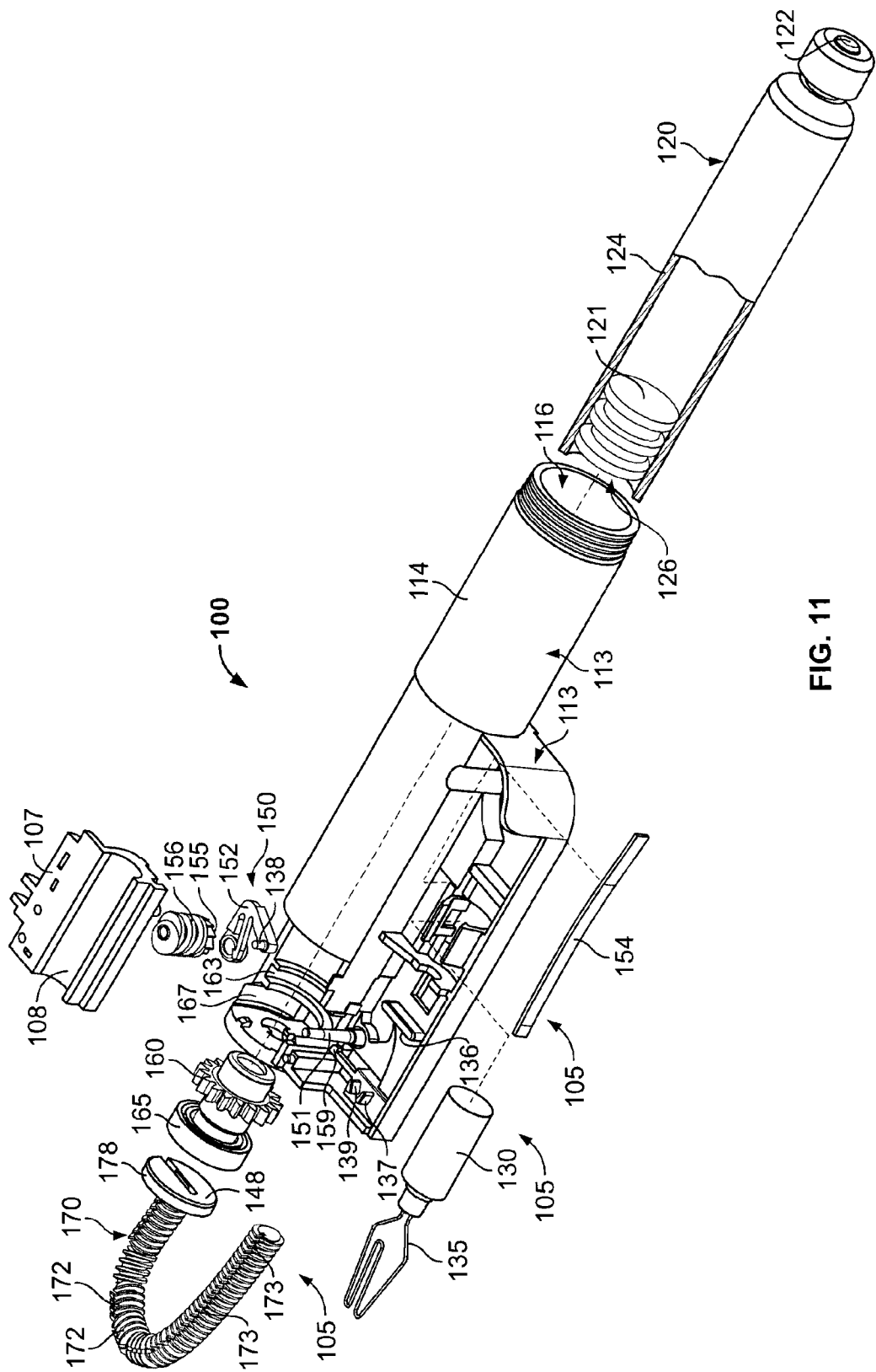
FIG. 11 is an exploded view of a portion of the pump device of the infusion pump system of FIG. 4.

Referring to FIG. 11, the pump device 100 includes a drive system 105 that is capable of accurately and incrementally dispensing fluid from the fluid cartridge 120 in a controlled manner. The drive system 105 may include a rotational motor 130 that is coupled to a string member 135. Briefly, the rotational motor 130 can be used to act upon the string member 135, thereby causing the string member 135 to adjust a pawl member 152 relative to a ratchet body 155 (e.g., a ratchet wheel integrally formed on the worm gear 156 in this embodiment). In some embodiments, the string member 135 is configured in a loop arrangement (e.g., looped around pin structures 136, 137, 138, and 139 in this embodiment). In these circumstances, the motion path of the string member 140 and the orientation of the string member 140 can be configured to provide an efficient mechanical advantage orientation during the desired motion of the adjustable pawl member 152. One of the pin structures 138 may be coupled to the adjustable pawl member 152 while the remaining pin structures 136, 137, and 139 are coupled to the frame portion 114 of the pump device 100. The spring device 154 can drive the pawl member from a reset position to a forward position, which incrementally rotates the ratchet wheel 155. As previously described, incremental rotation of the ratchet wheel 155 causes rotation of a drive wheel 160, which causes the incremental longitudinal advancement of a flexible piston rod 170. As the piston rod 170 is advanced into plunger chamber 126 (e.g., defined in this embodiment by the circumferential wall 124 of the fluid cartridge 120), the fluid in the cartridge 120 is forced from septum at the output end 122. Previously incorporated U.S. Provisional Application Ser. No. 60/720,411 also describes a number of configurations for the drive system in addition to the illustrative example depicted in FIG. 11 herein.

As shown in FIG. 11, some components of the drive system 105 can be retained by the frame portion 114, a cover mount 111 that is assembled to the frame portion 114, or a combination thereof. For example, the rotational motor 130, the string member 135, and the spring device 154 can be assembled into the frame portion 114 and then retained by the cover mount 111. The adjustable pawl member 152, the ratchet wheel 155, and the worm gear 156 can be assembled onto and axle 151 that is integrally formed with the frame portion 114 and then retained by the cover mount 111. A locking pawl 159 can be integrally formed with the frame portion 114 so as to align with the ratchet wheel 155 when the ratchet wheel 155 is assembled onto the axle 151. Also, the drive wheel 160 and an adjacent bearing 165 (to facilitate rotation of the drive wheel 160 relative to the frame portion 114) can be received in annular channels 163 and 167, respectively, of the frame portion 114. When the cover mount 111 is assembled to the frame portion 114, the cover mount 111 can restrict the radial or axial movement of the drive wheel 160 while permitting forward rotation of the drive wheel 160. In another example, the "unused" or retracted portion of the piston rod 170 may rest in a channel 113 defined in the top of the cover mount 111. In such a construction, the cover mount 111 and the frame portion 114 can collectively permit the desired motion of the components of the drive system 105 while reducing the likelihood of "backlash" movement or component dislodgement (which might otherwise occur, for example, when the pump device 100 is dropped to the ground).

The rotational motor 130 may comprise an electrically power actuator having a rotatable output shaft 132. In this embodiment, the rotational motor 130 can receive signals that cause the output shaft to rotate in a first rotational direction or in a second, opposite rotational direction. One example of a suitable rotational motor 130 is a coreless DC motor supplied by Jinlong Machinery of China. As previously described, the operation of the rotational motor 130 can be controlled by a controller device (e.g., removable controller device 200 or 300 as described in connection with FIGS. 1-10 or the like) via electrical signals communicated through one or more electrical contacts.

The string member 135 may be coupled to the rotational motor 130 so that actuation by the motor 130 causes the string member 135 to act upon the ratchet mechanism 150. One or more full rotations of the motor 130 can be translated into a tension force in the string member 135 that is applied to a pawl member 152, which (in this embodiment) is pivoted to a reset position by the tension force from the string member 135. As such, the string member 135 is coupled between the rotational motor 130 and the ratchet mechanism 150 so as to provide a reliable and consistent adjustment of the ratchet mechanism. In this embodiment, the string member 135 is coupled to the motor shaft 132 using a mechanical connector 133.

Still referring to FIG. 11, the ratchet mechanism 150 includes the pawl member 152 and the ratchet body 155, which in this embodiment is a ratchet wheel having a number of teeth along its circumferential surface. The pawl member 152 is adjustable between a reset position (refer, for example, to FIG. 12A) and a forward position (refer, for example, to FIG. 12B). In this embodiment, the adjustable pawl member 152 is pivotably coupled to about the axis of the axle 151 that receives the ratchet wheel 155 and the worm gear 156. A spring device 154 is also coupled to the pawl member 152 so as to urge the pawl member 152 toward the forward position. In this embodiment, the spring device 154 is in the form of a leaf spring that is fixed to the frame portion 114 at a first end portion and that is engaged with an abutment protrusion 157 (FIGS. 12A-C) of the pawl member 152 at a second end portion. Thus, when the pawl member 152 is adjusted to the reset position, the spring device 154 is flexed and stores potential energy that urges the pawl member 152 to return to the forward position and thereby drive the ratchet wheel 155 in a forward rotational direction. The locking pawl 159 coupled to the frame portion 114 prevents the ratchet wheel 155 from reverse motion. As such, the adjustable pawl member 152 can adjust from the forward position to the reset position to engage a new tooth of the ratchet wheel 155 while the ratchet wheel 155 remains in position due to the locking pawl 159.

It should be understood that the drive system 105 can employ one or more sensors to indicate when the pawl member 152 has reach the reset position or the forward position. For example, these sensors can be optical, magnetic, or contact type sensors. The sensors may be capable of transmitting signals that indicate when the location of the pin structure 138 or the pawl member 152 is detected. Such sensor signals may be transmitted to the first circuit 140, to the controller device 200 or 300, or a combination thereof.

Still referring to FIG. 11, in some embodiments the ratchet wheel 155 can be integrally formed with the worm gear 156 so that the incremental rotation of the ratchet wheel 155 is translated to the worm gear 156. Such rotation of the worm gear 156 causes a rotation of a drive wheel 160, which is rotatably mounted to the frame portion 114 of the pump device 100. The drive wheel 160 includes a central aperture having an internal thread pattern therein (not shown in FIG. 11), which mates is an external thread pattern on the flexible piston rod 170. Thus, the incremental motion provided by the ratchet mechanism 150, the string member 135, and the motor 130 causes the drive wheel 160 to incrementally rotate, which in turn translates to a linear advancement of the flexible piston rod 170.

Accordingly, in some embodiments, the piston rod 170 may undergo only forward or positive displacement as a result of drive system 105. For example, the drive system 105 substantially hinders the piston rod 170 from retracting or "backing up" in response to fluid pressure in the medicine cartridge 120 or other reversal forces. In such circumstances, the flexible piston rod 170 can be retracted only upon disassembly of the pump device 100 (e.g., to disengage the gears or the ratchet mechanism). In those embodiments in which the pump device 100 is intended to be disposable, the non-intended piston rod configuration (due to the drive system 105) may facilitate a "one time use" disposable pump device, thereby reducing the likelihood of failure due to non-intended repeated use of the disposable pump device.

The flexible piston rod 170 comprises a plurality of segments 172 serially connected by hinge portions so that the flexible piston rod 170 is adjustable from a curved shape to a noncurved shape. As previously described, the plurality of segments 172 and the interconnecting hinge portions can be integrally formed in one piece from a moldable material, including one or more polymer materials such as Nylon or POM. In this embodiment, the plurality of segments 172 comprise generally cylindrical segments that each include an exterior thread pattern along at least one cylindrical surface portion. The flexible piston rod 170 can include an anti-rotation structure that hinders the piston rod 170 from rotating with drive wheel 160 (thereby allowing the rotation of the drive wheel 160 to translate into a longitudinal motion of the piston rod 170). For example, in this embodiment, the flexible piston 170 includes a longitudinal channel 173 extending through each of the segments 172. The longitudinal channel 173 can engage a complementary protrusion on the frame portion 114 proximate the drive wheel 160 so that the flexible piston rod 170 is hindered from rotating when the drive wheel 160 turns relative to the frame portion 114. Accordingly, the longitudinal channel in each segment 172 aligns to form a keyway that receives a mating key (e.g., a protrusion) on the frame portion 114. In other embodiments, the anti-rotation structure may include a plurality of longitudinal channels 173 (with each channel capable of engaging an associated protrusion that acts as a key to hinder rotation while permitting longitudinal motion), one or more flat surfaces along each segment 172 (with the flat surface slidably engaging a complementary flat surface on the frame portion 114), or the like. A plunger connector 178 may be coupled to the leading end of the flexible piston rod 170 so as to abut against or connect with the plunger 121 in the plunger chamber 126 of the fluid cartridge 120. Previously incorporated U.S. Provisional Application Ser. No. 60/720,405 also describes a number of configurations for the flexible piston rod 170 in addition to the configuration illustrated in FIG. 11 herein.

Figure 12A:
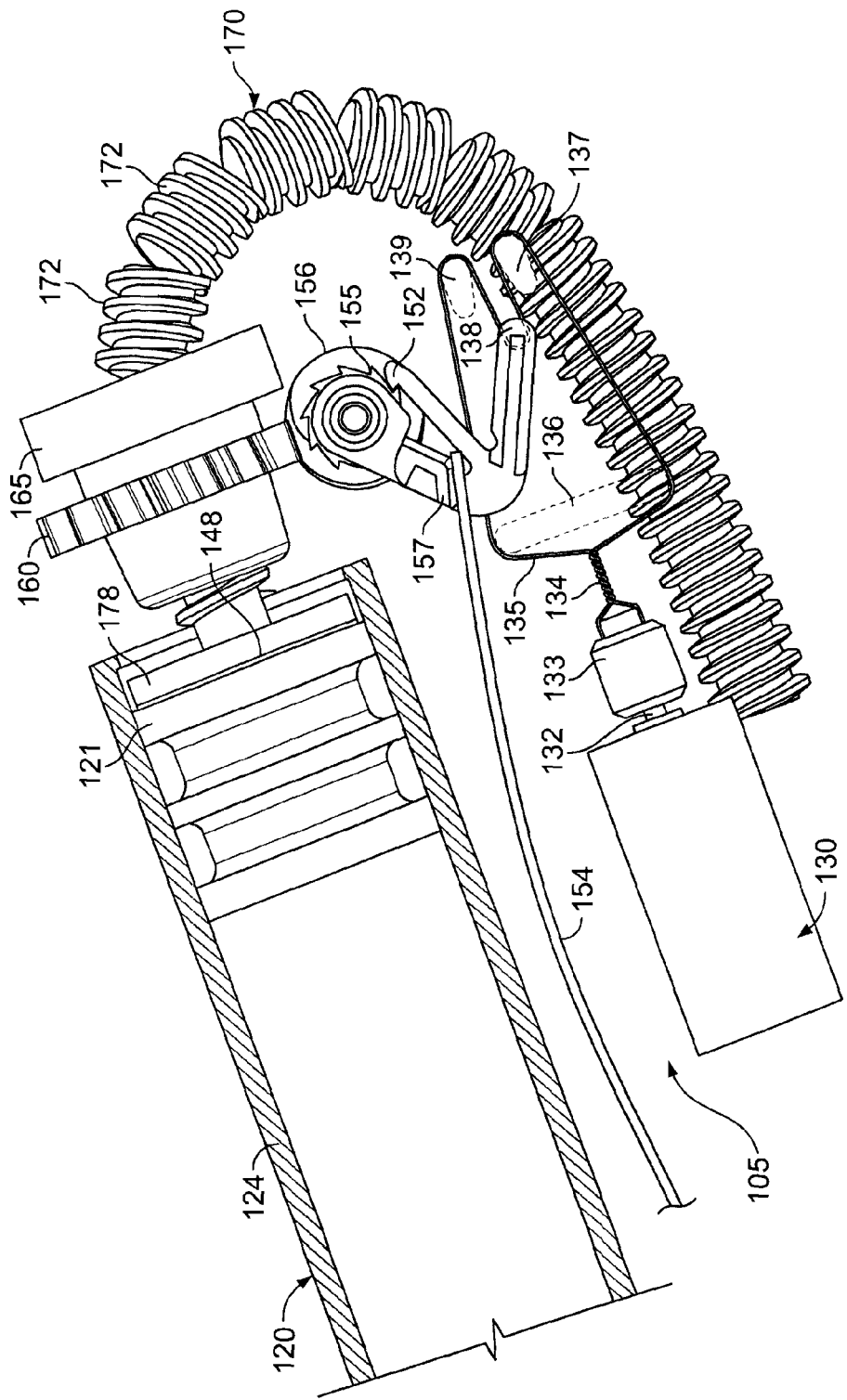
FIGS. 12A-C are perspective views of a portion of the pump device of FIG. 9.
Figure 12B:
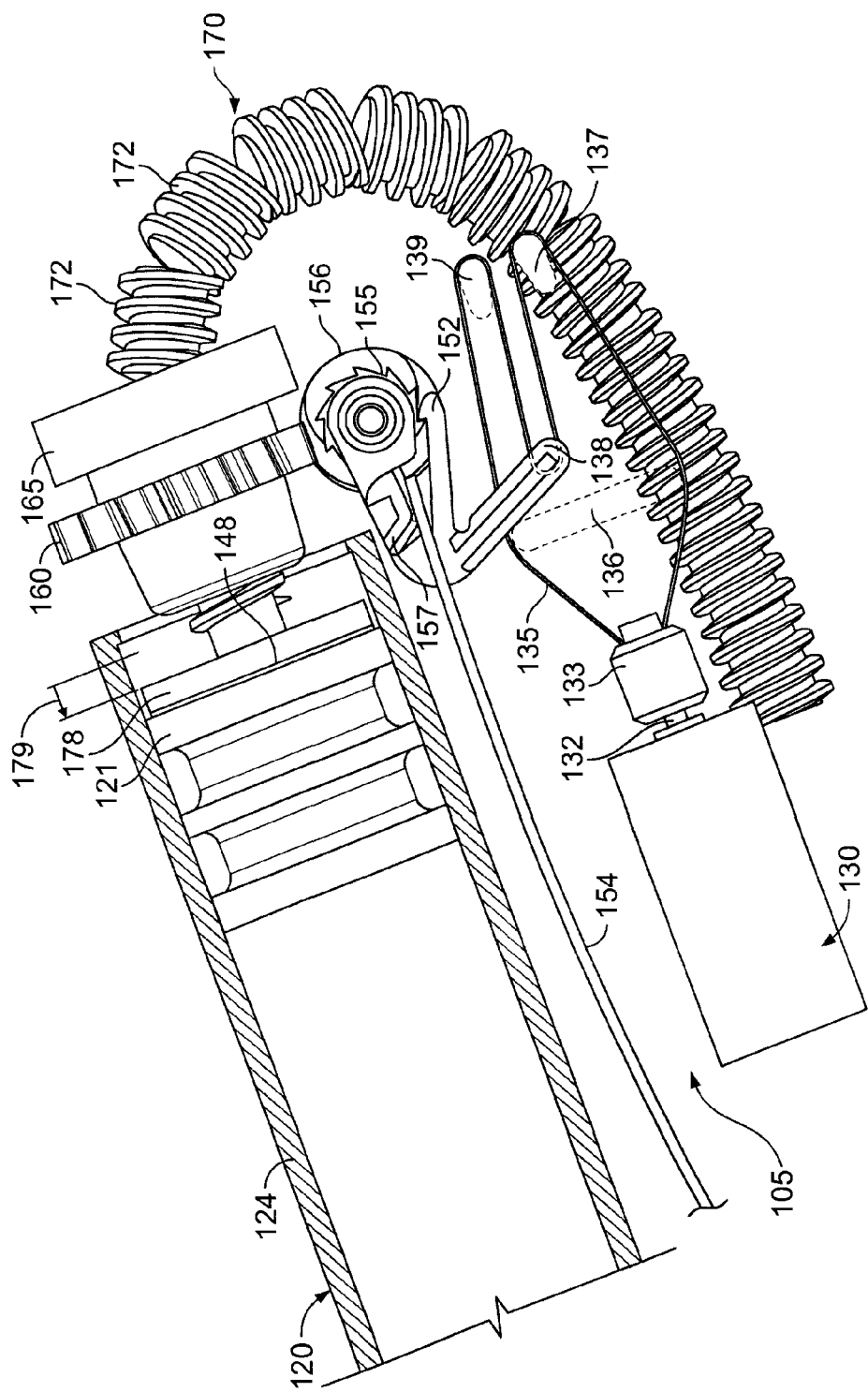
Figure 12C:
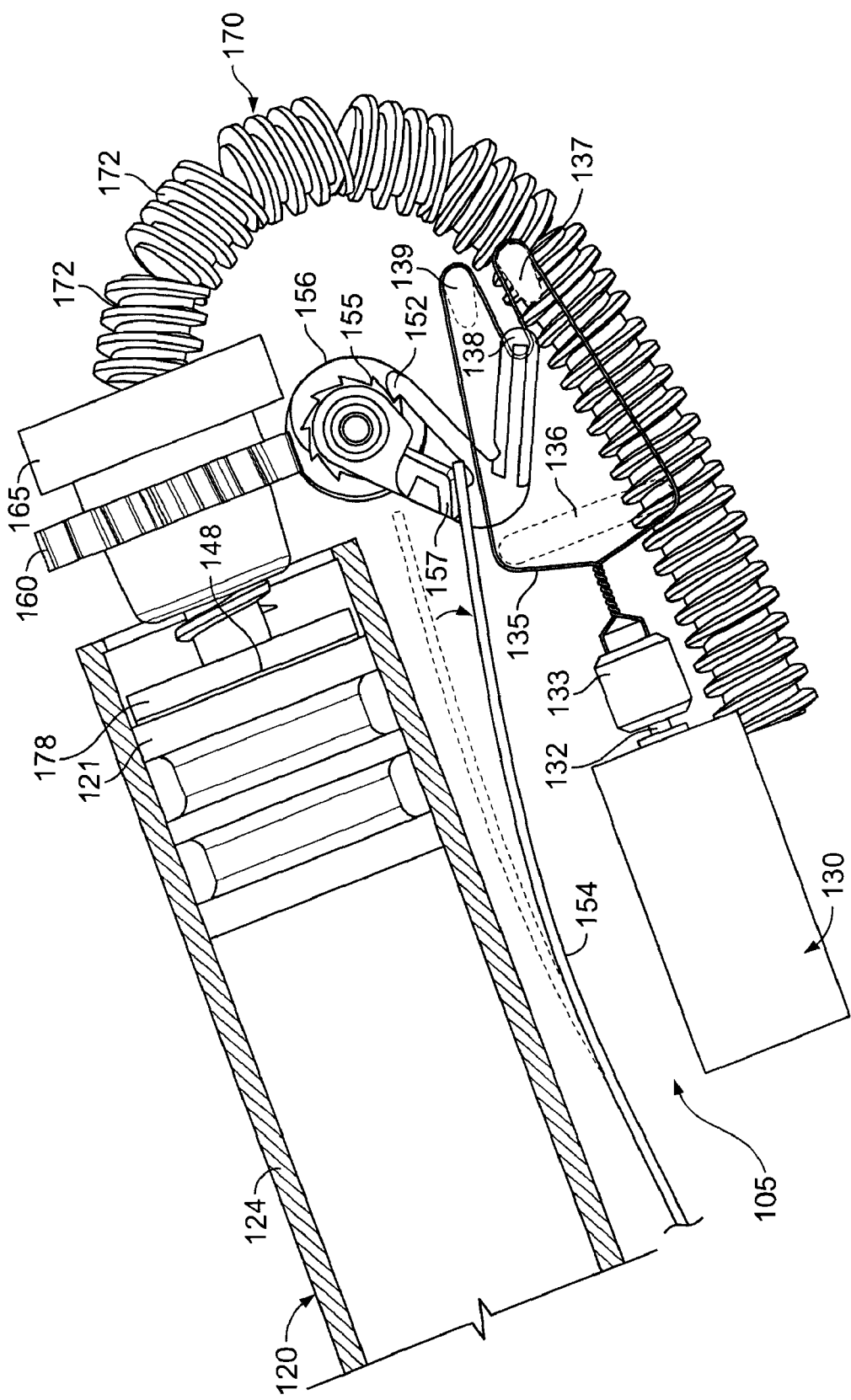

Referring now to FIGS. 12A-C, the incremental motion cycle of the drive system 105 may include rotation of the motor 130 so that the string member 135 transitions from a twisted state, to an untwisted state, and then again to a twisted state. Such a transition of the string member 135 can cause the pawl member 330 to adjust from the reset position (refer to FIG. 12A), to the forward position (refer to FIG. 12B), and back to the reset position (refer to FIG. 12C). The adjustment of the pawl member 152 from the reset position to the forward position drives the ratchet wheel 155 and worm gear 156, which incrementally rotates the drive wheel 160 and thereby advances the flexible piston rod 170 a longitudinal increment distance 179 (refer to FIG. 12B). In one example, the drive system 105 can advance the piston rod 170 a longitudinal increment distance 179 of about 16 microns or less (about 4 microns to about 12 microns, and preferably about 7 microns to about 8 microns) for each incremental motion cycle of the motor 130, string member 135, and ratchet mechanism 150 as previously described herein.

Referring to FIG. 12A, in this embodiment of the incremental motion cycle, the pawl member 352 begins at the reset position with the string member 135 in a twisted configuration at string portion 134. When the adjustable pawl member 152 is in the reset position as shown in FIG. 12A, it is capable of engaging a tooth of the ratchet wheel 155. In this embodiment, the string member 135 is arranged in a loop configuration around pin structures 136, 137, 138, and 139. One of the pin structures 138 is coupled to the adjustable pawl member 152 while the remaining pin structures 136, 137, and 139 are integrally formed with the frame portion 114 of the pump device 100 (pin structures 136, 137, and 139 are shown in dotted lines to represent their location on the frame portion 114 (not shown in FIGS. 12A-C)). Also, the pin structure 136 exemplifies how a single pin structure can have two sliding surfaces that oppose one another, thereby functioning similar to a configuration having two different pins. As shown in FIG. 12A, when the motor 130 rotates, a portion 134 the string member 135 twists upon itself, thus drawing the pin structure 138 toward the stationary pin structures 137 and 139. The orientation of the stationary pin structures 137 and 139 relative to the pin structure 138 (connected to the pawl member 152) can be configured to provide an efficient mechanical advantage for the tension force applied by the string member 140 during the desired motion of the adjustable pawl member 152.

Referring to FIG. 12B, in response to the controller device 200 or 300 transmitting one or more control signals to initiate the cycle, the rotational motor 130 may begin to rotate in a first rotational direction that unwinds the string member 140, thereby permitting the spring device 154 to drive the pawl member 152 toward the forward position (refer to FIG. 12B). When the adjustable pawl 152 is driving the ratchet wheel 155 in the forward rotational direction, the potential energy of the spring device 154 is being translated to kinetic energy for the motion of the pawl member 152 and the ratchet wheel 155. Such an adjustment of the pawl member 152 from the reset position to the forward position drives the ratchet wheel 155 and the integrally formed worm gear 156. The incremental rotation of the worm gear 156 results in an incremental rotation by the drive wheel 160, which advances the flexible piston rod 170 the longitudinal increment distance 179. Such an incremental advancement of the flexible piston rod 170 may cause a predetermined volume of fluid to be dispensed from the cartridge 120 (FIG. 11).

Referring to FIG. 12C, the rotational motor 130 continues to rotate in the first rotational direction so that after the pawl member 152 reaches the forward position, the string member 135 begins to twist in the opposite orientation. Such twisting of the string member 135 causes a tension force that overcomes the bias of the spring device 154 and adjusts the pawl member 152 toward the reset position. When the adjustable pawl member 152 reaches the reset position, as shown in FIG. 12C, the pawl member 152 is capable of engaging a new tooth of the ratchet wheel 155. The locking pawl 159 (shown in FIG. 11) prevents the ratchet wheel 155 from rotating in a reverse (non-forward) rotational direction while the adjustable pawl member 152 is shifting back to the reset position. Such an adjustment of the pawl member 152 back to the reset position causes the spring device 154 to flex (as shown in FIG. 12C), thereby storing potential energy to drive the adjustable pawl member 152 and ratchet wheel 155 in a subsequent cycle. After the pawl member 152 reaches the reset position, the rotational motor 130 stops rotating in the first rotational direction and the pawl member 152 remains at rest in the reset position (refer to FIG. 12C). In the event of a subsequent cycle, the rotational motor 130 would begin the cycle by rotating in a second rotational direction (opposite the first rotational direction) so as to unwind the string member 135 yet again. This pattern of cycles may continue until the piston rod 170 has reached the limit of its longitudinal travel.

It should be understood, that in other embodiments, the incremental motion cycle may begin with the pawl member 152 starting at the forward position (refer to FIG. 12B). In such circumstances, the rotation motor 130 would rotate in a first rotational direction to twist the string 135 until the pawl member 152 is moved to the reset position (refer to FIG. 12C), and then the rotational motor 130 would rotate in a second, opposite rotational direction to unwind the string member 135 until the pawl member 152 returns to the forward position (refer again to FIG. 12B).

The string member 135 may comprise braided filaments that are capable of enduring repeated twisting sequences of the string member 135. For example, the braided filaments may comprise one or more polymer materials, such as PET (e.g., DTex Dyneema material available from Honeywell, Inc.). Such braided filament string members are capable of enduring the torsion and frictional forces associated with undergoing thousands of cycles of twisting as described above in connection with FIGS. 12A-C. The string member 135 can be formed to have an outer diameter of about 0.02 mm to about 0.07 mm, and preferably about 0.05 mm. Also, in some embodiments, the string member 135 may comprise braided filaments that are arranged around a centrally disposed thin wire filament (e.g., comprising a polymer material or a metallic material) having a diameter of about 0.02 mm or less, which is also capable of enduring the repeated twisting sequences of the string member 135. Such a construction may permit the outer filament surfaces to frictionally engage one another during the twisting process while the filament surfaces contacting the centrally disposed thin wire are exposed to a reduced friction load.

Figure 13:
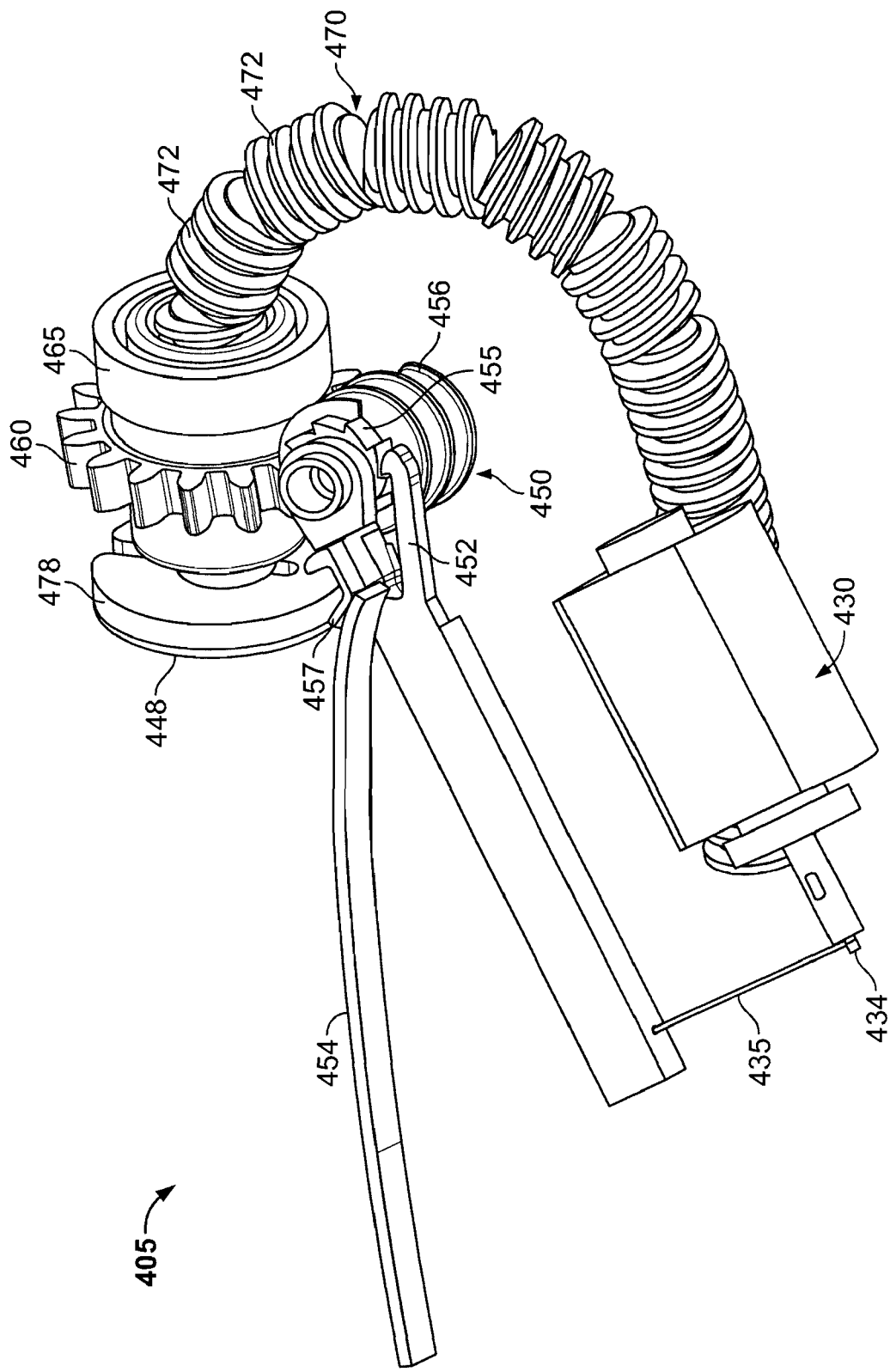
FIG. 13 is a perspective view of a portion of a pump device for an infusion pump system, in accordance with some embodiments.

Referring now to FIG. 13, some embodiments of drive system 405 for the pump device can include a string member and a rotational motor like the previously described embodiments, except that the string member 435 is configured to wind (or unwind or both) around a spindle device 434. Such a configuration may reduce the torsion and friction loads upon the string member material while providing a tension force to adjust the ratchet mechanism. Moreover, the spindle configuration may further reduce the space requirements for drive system 405 in the pump housing, thereby providing a reliable and compact infusion pump system that is portable and wearable by the user.

As shown in FIG. 10, the spindle device 434 can be coupled to a rotational motor 430 so that the spindle device 434 rotates with the motor shaft. A string member 435 can be attached to the spindle device 434 so that the string member 435 winds or unwinds around the spindle device 434 in response to the rotation of the motor 430. It should be understood from the description herein that the string member 435 may comprise braided filaments that are capable of enduring repeated winding sequences of the string member 435. The string member 435 is also coupled to the ratchet mechanism 450, which provides incremental motion to thereby advance the piston rod 470. The ratchet mechanism 450 includes the pawl member 452 and the ratchet body 455, which in this embodiment is a ratchet wheel having a number of teeth along its circumferential surface. The pawl member 452 is adjustable between a reset position and a forward position. For example, the rotational motor 430 may be activated to rotate the spindle device 434 and thereby wind the string member 435 (as previously described), and the string member 435 then applies a tension force that adjusts the pawl member 452 to the reset position. In the reset position, the pawl member 452 can engage one or more new teeth of the ratchet wheel 455. A spring device 454 is also coupled to the pawl member 452 so as to urge the pawl member 452 toward the forward position. This spring force causes the pawl member 452 to drive the ratchet wheel 455 an incremental amount in a forward rotational direction. Similar to the embodiments previously described in connection with FIG. 12A, a locking pawl prevents the ratchet wheel 455 from reverse motion. As such, the adjustable pawl member 452 can adjust from the forward position to the reset position to engage a new tooth of the ratchet wheel 455 while the ratchet wheel 455 remains in position due to the locking pawl 459.

Accordingly, in one incremental motion cycle, the pawl member 452 may start at the reset position with the string member 435 wound around the spindle device 434. In response to the controller device 200 or 300 (FIG. 4) transmitting one or more control signals to initiate the cycle, the rotational motor 430 may begin to rotate in a first rotational direction that unwinds the string member 435 from the spindle device 434, thereby permitting the spring device 454 to force the pawl member 452 toward the forward position. The rotational motor 430 continues to rotate in the first rotational direction so that after the pawl member 452 reaches the forward position, the string member 435 begins to wind around the spindle device 434 in the opposite orientation. Such winding of the string member 435 causes a tension force that overcomes the bias of the spring device 454 and adjusts the pawl member 452 toward the reset position. After the pawl member 452 reaches the reset position, the rotational motor 430 stops rotating in the first rotational direction and the pawl member 452 remains at rest in the reset position. In the event of a second cycle, the rotational motor 430 would begin the cycle by rotating in a second rotational direction (opposite the first rotational direction) so as to unwind the string member 440 from the spindle device 442 yet again.

In other embodiments, the incremental motion cycle may begin with the pawl member 452 starting at the forward position. In such circumstances, the rotational motor 430 would rotate in a first rotational direction to wind the string member 435 around the spindle device 434 until the pawl member 452 is moved to the reset position (as shown in FIG. 10), and then the rotational motor 430 would rotate in a second, opposite rotational direction to unwind the string member 435 from the spindle device 434 until the pawl member 452 returns to the forward position.

It should be understood that the drive system 405 can be contained in the housing structure 110 of the pump device 100 in a compact manner so that the pump device 100 is portable, wearable, concealable, or a combination thereof. Similar to previously described embodiments, the pump device 100 can be part of an infusion pump system 10 or 20 in which the pump device 100 communicates with a controller device, including but not limited to the removable controller device 200 or 300 described in connection with FIGS. 1-10. The controller device 200 or 300 can communicate control signals to the drive system 405 or other components of the pump device so as to initiate or end the incremental motion cycle of the drive system 405.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
a pump device including: a pump housing that defines a space to receive an insulin medication and a drive system to dispense the insulin medication when received by the pump housing; and
a controller device that is releasably mounts with the pump device to electrically connect with at least a portion of the drive system, the controller device including: a controller housing that is matable with the pump housing so as to form a releasable mechanical connection in which that the space to receive the insulin medication is positioned rearward of a rear face of the controller housing and a user interface arranged on the controller housing such that a display of the user interface is positioned along a front face of the controller housing that is opposite from the rear face,
wherein the user interface is mounted to the controller housing structure that is matable with the pump housing structure so that the user interface is viewable to a user while looking toward the pump device when the releasable mechanical connection is formed.

2. The system of claim 1, wherein the pump housing includes an interior wall that defines the space to slidably receive a pre-filled insulin medication cartridge insertable through an opening defined by the pump housing.

3. The system of claim 2, wherein the drive system of the pump device comprises a flexible piston rod that is incrementally advanced toward the pre-filled insulin medication cartridge when the pre-filled insulin medication cartridge is received by the pump housing.

4. The system of claim 1, wherein the pump device and the controller device, when releasably mounted together, provide a hand-graspable portable unit.

5. The system of claim 1, wherein the controller device electrically communicates signals to at least a portion of the drive system of the pump device when the controller device and pump device are releasably mounted together.

6. The system of claim 5, wherein the controller device electrically communicates signals via a hard-wired electrical connection including one or more electrical contacts arranged on the pump device that mate with one or more electrical contacts arranged on the controller device.

7. The system of claim 1, wherein the pump device includes a battery that transmits electrical energy to a rechargeable power source disposed in the controller device, and wherein the rechargeable power source provides energy to at least a portion of the drive system of the pump device.

8. The system of claim 1, wherein the pump device houses a battery that transmits electrical energy to a rechargeable power source housed in the controller device when the pump device is removably attached to the controller device, the battery providing energy to charge the rechargeable power source in the controller device over a period of time.

9. The system of claim 8, wherein the rechargeable power source in the controller device periodically discharges bursts of electrical current to power the drive system of the pump device when the pump device is removably attached to the controller device.

10. The system of claim 1, wherein the drive system of the pump device comprises a rotational motor that acts upon a ratchet mechanism, wherein one or more full rotations of the rotational motor causes a pawl member of the ratchet mechanism to partially pivot.

11. The system of claim 10, wherein the rotational motor comprises a reversible motor that outputs one or more full rotations in a first direction and in a second opposite direction.

12. The system of claim 10, wherein the rotational motor receives electrical energy from a power source that is arranged in the controller device and outside of the pump device.

13. The system of claim 1, wherein the user interface includes a display and one or more user-selectable buttons, the display of the user interface communicates time and date information to a user when no button has been actuated for a period of time.

14. A medical infusion pump system, comprising:
a pump device including: a pump housing that defines a space to receive an insulin medication and a drive system to dispense the insulin medication when received by the pump housing,
wherein the drive system of the pump device comprises a rotational motor that acts upon a ratchet mechanism, wherein one or more full rotations of the rotational motor causes a pawl member of the ratchet mechanism to partially pivot,
wherein the rotational motor acts upon the ratchet mechanism to cause an incremental movement of the ratchet mechanism, the incremental movement of the ratchet mechanism driving a piston rod to advance only in a positive longitudinal direction; and a controller device that is releasably mounts with the pump device to electrically connect with at least a portion of the drive system, the controller device including: a controller housing that is matable with the pump housing so as to form a releasable mechanical connection and a user interface arranged on the controller housing, wherein the user interface is mounted to the controller housing structure that is matable with the pump housing structure so that the user interface is viewable to a user while looking toward the pump device when the releasable mechanical connection is formed.

15. The system of claim 1, wherein the user interface includes a display and one or more user-selectable buttons, the display of the user interface communicating menu options to a user when the user actuates the one or more buttons.

16. The system of claim 15, wherein at least one of the menu options communicated by the user interface provides data indicative of a insulin medication dispensing rate.

17. The system of claim 15, wherein at least one of the menu options communicated by the user interface provides data indicative of a total amount of insulin medication dispensed in a given time period.

18. The system of claim 15, wherein at least one of the menu options communicated by the user interface provides data indicative of an amount of insulin medication remaining in the pump housing.

19. The system of claim 14, wherein the controller device electrically communicates signals to at least a portion of the drive system of the pump device when the controller device and pump device are releasably mounted together.

20. The system of claim 19, wherein the controller device electrically communicates signals via a hard-wired electrical connection including one or more electrical contacts arranged on the pump device that mate with one or more electrical contacts arranged on the controller device.

21. The system of claim 14, wherein the pump device includes a battery that transmits electrical energy to a rechargeable power source disposed in the controller device, and wherein the rechargeable power source provides energy to at least a portion of the drive system of the pump device.

22. The system of claim 14, wherein the rotational motor comprises a reversible motor that outputs one or more full rotations in a first direction and in a second opposite direction.

23. The system of claim 14, wherein the rotational motor receives electrical energy from a power source that is arranged in the controller device and outside of the pump device.

24. A medical infusion pump system, comprising:
a pump device including:
    a pump housing including an interior wall that at least partially defines a space to slidably receive a pre-filled insulin medication cartridge extending a majority of the length of the pump housing;
    a drive system including an electrically powered actuator arranged in the pump housing to dispense the insulin medication when the pre-filled insulin medicine cartridge is slidably received in the pump housing;
    one or more electrical contacts disposed on the pump housing; and
a removable controller device including:
    a controller housing that is removably attachable to the pump housing in a fixed relationship;
    one or more electrical contacts disposed on the controller housing, the electrical contacts of the controller device being engageable with the electrical contacts of the pump device when removably attached so that the controller device electrically communicates with the drive system of the pump device;
    a user interface coupled to the controller housing, the user interface including a display and one or more user-selectable buttons
wherein the pump device and the controller device, when removably attached, provide a portable unit.

25. The system of claim 24, wherein the user interface is coupled to the controller housing structure that is removably attachable with the pump housing structure such that the user interface is viewable to a user while looking toward the pump device.

* * * * *